(12) United States Patent
Regadas

(10) Patent No.: US 11,051,821 B2
(45) Date of Patent: *Jul. 6, 2021

(54) SURGICAL STRING APPLICATOR FOR ANASTOMOSIS SURGERY

(71) Applicant: Unique Surgical Innovations LLC, Parkland, FL (US)

(72) Inventor: Francisco Sergio Pinheiro Regadas, Fortaleza-Ceara (BR)

(73) Assignee: Unique Surgical Innovations LLC, Parkland, FL (US)

( * ) Notice: Subject to any disclaimer, the term of this patent is extended or adjusted under 35 U.S.C. 154(b) by 225 days.

This patent is subject to a terminal disclaimer.

(21) Appl. No.: 16/373,432

(22) Filed: Apr. 2, 2019

(65) Prior Publication Data

US 2019/0223873 A1 Jul. 25, 2019

Related U.S. Application Data

(60) Division of application No. 15/351,987, filed on Nov. 15, 2016, now Pat. No. 10,285,706, which is a
(Continued)

(51) Int. Cl.
| | |
|---|---|
| *A61B 17/12* | (2006.01) |
| *A61B 17/04* | (2006.01) |
| *A61B 17/11* | (2006.01) |
| *A61B 17/115* | (2006.01) |
| *A61B 17/132* | (2006.01) |

(Continued)

(52) U.S. Cl.
CPC .......... *A61B 17/12* (2013.01); *A61B 17/0469* (2013.01); *A61B 17/0483* (2013.01); *A61B 17/1114* (2013.01); *A61B 17/1155* (2013.01); *A61B 17/12013* (2013.01); *A61B 17/1322* (2013.01); *B65B 13/027* (2013.01); *A61B 17/04* (2013.01); *A61B 17/12009* (2013.01); *A61B 2017/00473* (2013.01)

(58) Field of Classification Search
CPC . A61B 17/0469; A61B 17/0483; A61B 17/12; A61B 17/12009; A61B 17/1322; A61B 17/115; A61B 17/1155; A61B 17/11; A61B 17/1114; A61B 2017/1107; A61B 2017/1142; A61B 2017/1103
See application file for complete search history.

(56) References Cited

U.S. PATENT DOCUMENTS

2009/0012538 A1* 1/2009 Saliman ............. A61B 17/0491
606/145

* cited by examiner

*Primary Examiner* — Majid Jamialahmadi
(74) *Attorney, Agent, or Firm* — CUSPA Technology Law Associates, P.A.; Yi Li

(57) ABSTRACT

A surgical string applicator for anastomosis surgery is provided. The surgical string applicator includes an elongate shaft; a string applying assembly including a pair of opposing jaws connected to the elongate shaft, each jaw having an opening at its distal end, one or more surgical strings housed in the jaws in a form of an open loop with one end of the surgical string at the distal end of one jaw and an opposing end of the surgical string at the distal end of the other jaw, and a string fastening mechanism adapted to engage and fasten the surgical string around a tubular organ; and a handle portion including control mechanisms adapted to open and close at least one of the jaws and to actuate the string fastening mechanism. Further provided is an intralumenal position guide to be used together with the surgical string applicator.

15 Claims, 24 Drawing Sheets

Related U.S. Application Data continuation of application No. 13/058,521, filed as application No. PCT/US2009/056411 on Sep. 9, 2009, now Pat. No. 9,526,502, which is a continuation-in-part of application No. 12/283,152, filed on Sep. 10, 2008, now Pat. No. 8,211,129.

(51) Int. Cl.
*B65B 13/02* (2006.01)
*A61B 17/00* (2006.01)

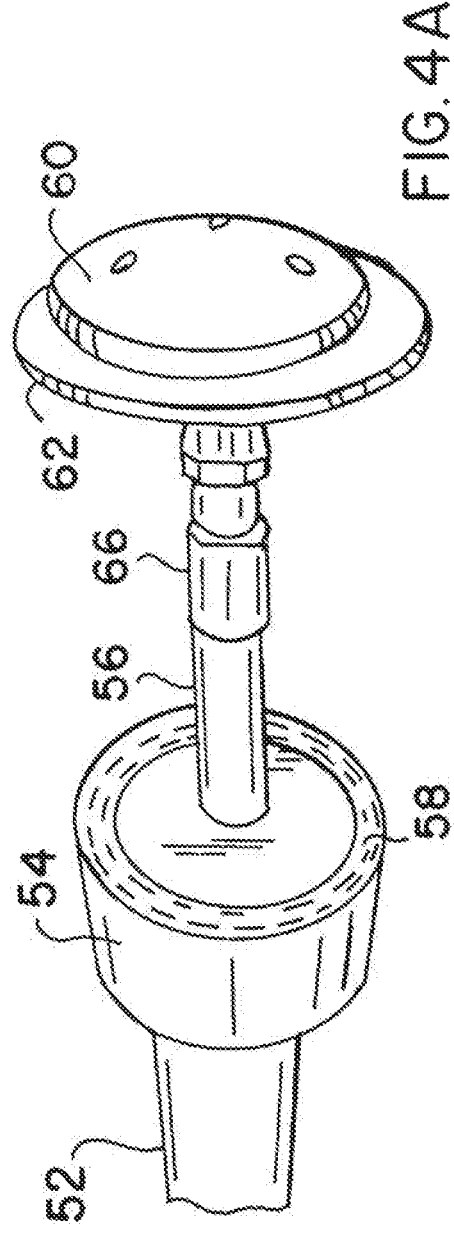
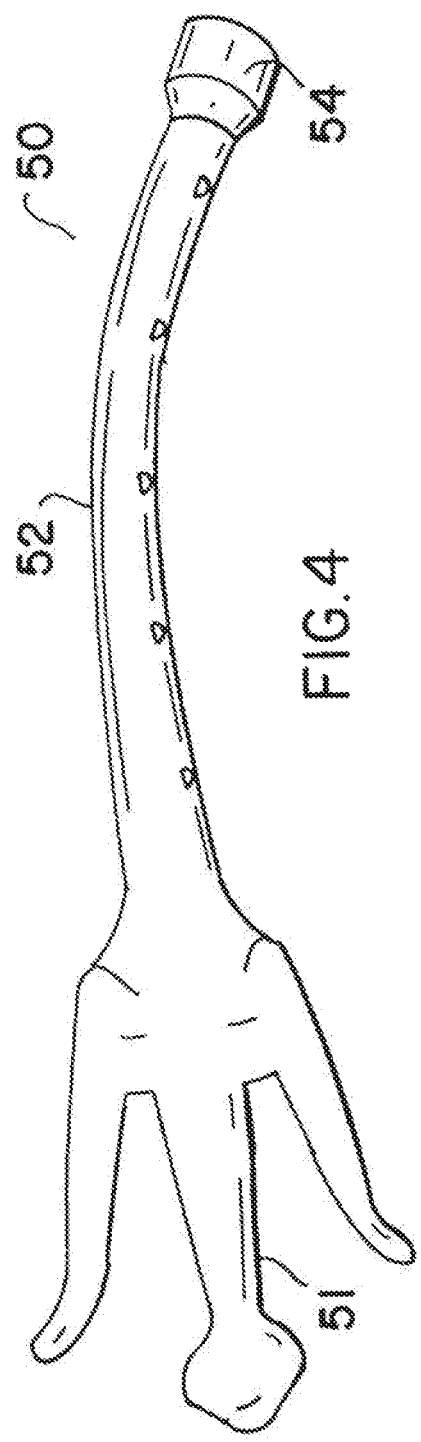
FIG. 4A
FIG. 4

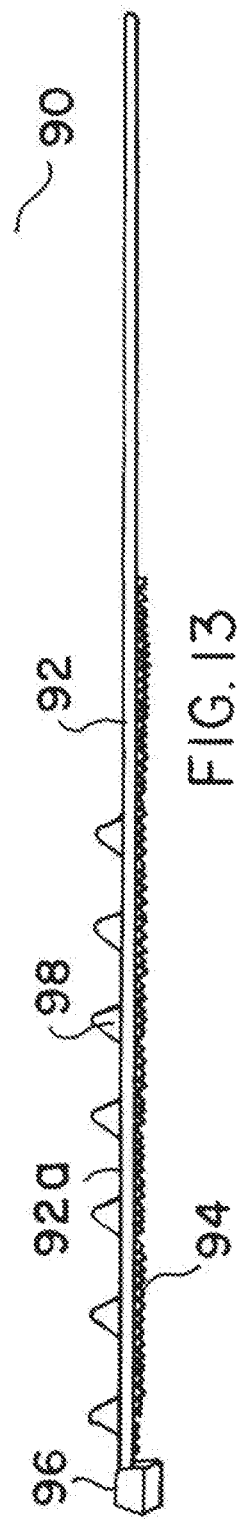
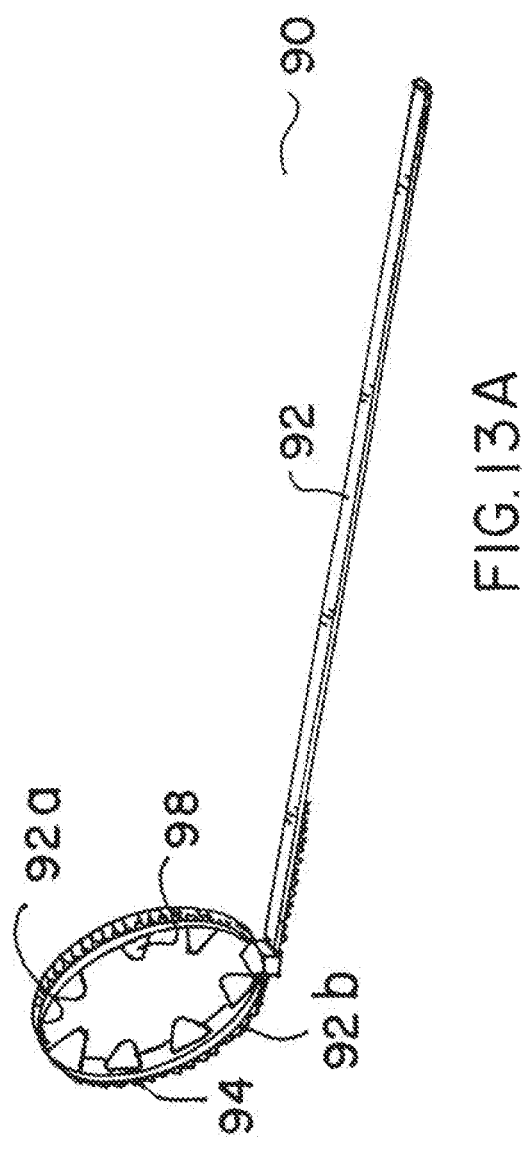

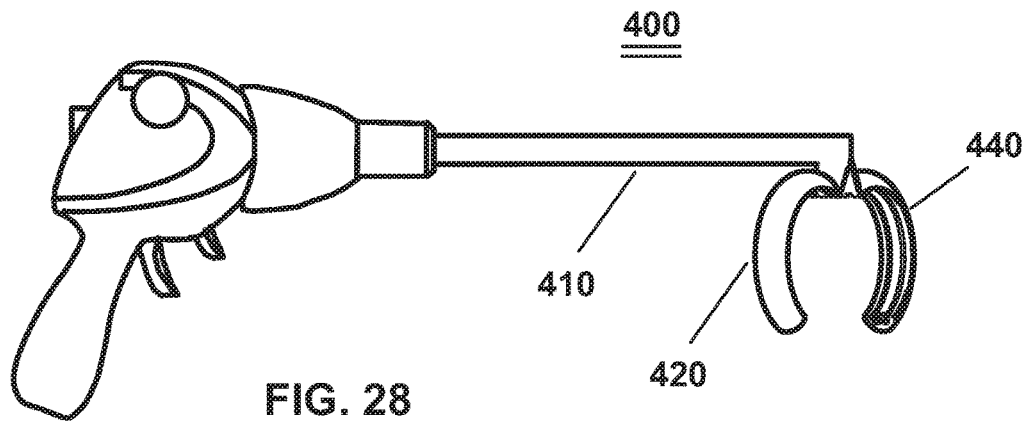
FIG. 28
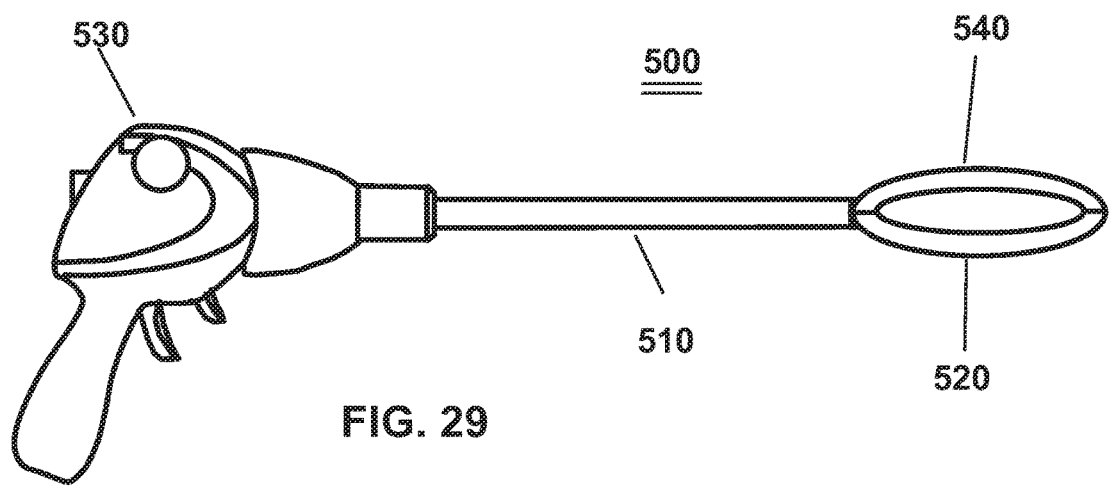
FIG. 29
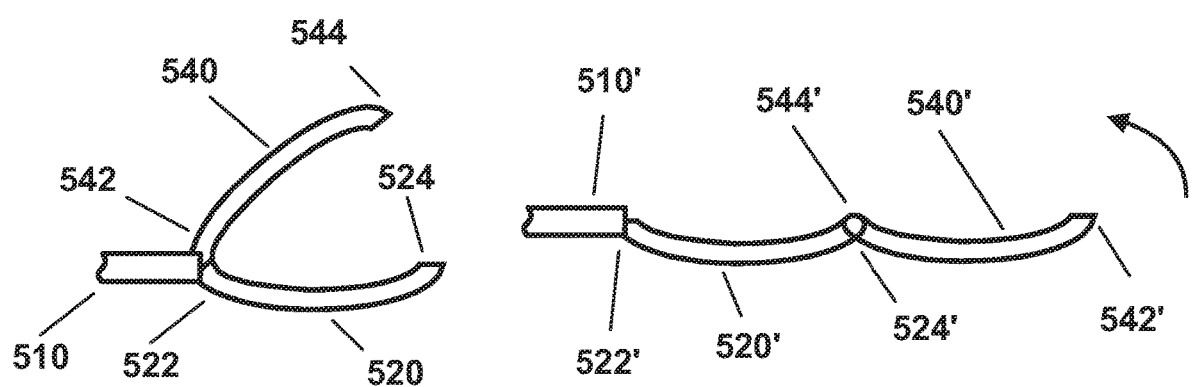
FIG. 29A
FIG. 29B

SURGICAL STRING APPLICATOR FOR ANASTOMOSIS SURGERY

CROSS REFERENCE TO RELATED APPLICATION

This application is a division of patent application Ser. No. 15/351,987 filed Nov. 15, 2016, now issued as U.S. Pat. No. 10,285,706, which is a continuation of patent application Ser. No. 13/058,521 filed Feb. 10, 2011, now issued as U.S. Pat. No. 9,526,502, which is a national phase of PCT application No. PCT/US2009/056411, filed Sep. 9, 2009, which is a continuation-in-part of patent application Ser. No. 12/283,152, filed Sep. 10, 2008, now issued as U.S. Pat. No. 8,211,129. All parent patent applications are hereby incorporated by reference in their entireties.

FIELD OF THE INVENTION

The present invention relates to a surgical device and the method of use for anastomosis surgery, particularly relates to a surgical string applicator for anastomosis surgery.

BACKGROUND OF THE INVENTION

Surgical anastomosis is to join together two hollow organs, usually to restore continuity after resection, or less commonly to bypass an unresectable disease process. Anastomosis is typically performed on blood vessels including arteries and veins, gastrointestinal tract including esophagus, stomach, small intestine, colon, rectum, bile ducts and pancreas, urinary tract including ureters, urinary bladder and urethra, and fallopian tubes.

Colorectal anastomosis surgery is one of the most commonly performed intestinal surgical anastomosis ("Surgical Treatment of Rectal Cancer", Bleday R. et al, *The ASCRS Textbook of Colon and Rectal Surgery*, 2007, Springer, New York, page 413-436). Historically, laparotomies (open surgery) are performed. During the surgical procedure, after dissecting the colon from the rectum and resecting the diseased segment, such as cancerous tissue, from the colon, the two dissected open ends are manually sutured together. This is a time-consuming and often very difficult process. Particularly, when the diseased segment is located at the extreme low end of the rectum, which is deep in the lowest part of the pelvis, it can be extremely difficult to manually access the dissecting site. Under such circumstances, the surgery has a higher risk of anastomotic leakage, which causes severe infectious complications and often requires reoperation for an abscess, fistula, peritonitis, or a permanent colostomy (bringing the colon out through the abdominal wall so that waste can be collected in a bag rather than by evacuating stool through the anus).

In the past few decades, linear and circular surgical staplers have been developed and mechanically stapled methods are increasingly used in colorectal surgeries. The stapled colorectal anastomosis is faster and often more convenient for the surgeon to operate. However, various complications have been associated with stapled colorectal anastomosis. In the stapled colorectal anastomosis procedure, the linear and circular stapled areas overlap, which increases the risk of leakage at the interface between the linearly stapled area and the circularly stapled area. It has been reported in numerous publications that the instances of colorectal strictures in stapled anastomosis are statistically higher than in sutured colorectal anastomosis ("Stapled anastomosis after colorectal resection for benign and malignant disease", Raidoo, S N et al, S Afr Med J. 1984, 66(21):819-21; "Handsewn vs. stapled anastomosis in colon and rectal surgery: a meta-analysis", MacRae, H M et al, Dis Colon Rectum. 1998, 41(2):180-9; "Results of reoperations in colorectal anastomotic strictures", Schlegel R D et al, Dis Colon Rectum. 2001, 44(10): 1464-8; "Anastomotic dehiscence in colorectal surgery, Analysis of 1290 patients", Pronio, A et al, Chir Ital. 2007, 59(5): 599-609.)

More recently, laparoscopic colorectal anastomosis surgery method has been developed. With the laparoscopic method, a small cut is made on the lower abdomen, an endoscopic linear cutting stapler is inserted into pelvic cavity to transect the rectum, and a circular stapler is subsequently used to perform a colorectal colocolic, ileorectal, or ileoanal anastomosis. Laparoscopic colorectal anastomotic procedures have the advantages of a small wound, less trauma, and an overall faster patient recovery. However, the inherent problems from the stapled colorectal anastomosis remain in laparoscopic stapled anastomosis procedures. Furthermore, in laparoscopic colorectal anastomosis procedures, the head of the linear stapler can only be operated in a range from 0° to about 45° from the shaft. When the site for transection is in the distal rectum, it can be very difficult to transect the rectum with the linear cutting stapler. Typically, two or three sequential progressive stapling and cutting cartridges are required to transect the lower rectum. Each cut requires removing the stapler from the abdominal cavity and loading a new cartridge to the head of the stapler. This multifire approach is not only time consuming, but also a higher risk of complications and anastomotic leakage.

Therefore, there exists a strong need for improved tools and surgical methods to reduce the risks associated with existing sutured and stapling methods for anastomosis to improve operability under difficult conditions, to improve quality and outcome of the anastomosis and to reduce the cost of an anastomosis surgery.

SUMMARY OF THE INVENTION

In one aspect, the present invention provides a surgical string applicator for anastomosis surgery. In one embodiment, the surgical string applicator comprises an elongate shaft having proximal and distal ends; a string applying assembly comprising a first and a second opposing jaws connected to the distal end of the shaft, at least one of the jaws having a curved shape with a concave inner side and having one or more grooves along an inner surface of the curved jaw, each of the grooves configured to receive therein at least a portion of a surgical string to be applied, and a string fastening mechanism adapted to engage and fasten the surgical string; and a handle portion connected to the proximal end of the shaft; the handle portion including control mechanisms adapted to open and close at least one of the jaws, and to actuate the string fastening mechanism. The surgical string applicator further includes a blade disposed within one of the jaws, adapted to dissect tissue fastened by the surgical strings.

In one embodiment, the proximal ends of the first and second jaws are connected to the distal end of the elongated shaft, and at least one of the jaws pivots at the proximal end thereof. In another embodiment, a proximal end of one of the jaws is connected to the elongated shaft and distal ends of the first and second jaws are pivotally connected to each other.

In one embodiment, the surgical string applicator includes two parallel grooves at least one of the jaws with a predetermined distance therebetween, and further comprises two surgical strings, each disposed within one of the grooves with a tail thereof disposed in a distal end of one of the jaws and a portion thereof disposed in a distal end of opposing jaws.

In one embodiment, the string fastening mechanism comprises a tie gripping member disposed within one of the jaws adapted to grip a tail of the surgical string, and a tightening mechanism which includes a driving mechanism to pull the tail of the surgical string. In a further embodiment, the surgical string applicator further includes a pair of head-tail connected zip-ties disposed within one of the grooves of the jaws, wherein a first zip-tie has a tail thereof disposed at a distal end of one of the jaws, and a second zip-tie has a head thereof disposed at a distal end of opposing jaw and has a tail thereof passing through and locked with a head of the first zip-tie, and coupled with the tightening mechanism for fastening the loop formed by the two head-tail connected zip-ties.

In one embodiment, one end of one of the jaws includes an opening adapted to receive a tail portion of a surgical string. The opposing ends of the jaws are so configured that when the jaws move from an open position to a close position, a tail of the surgical string disposed at one of the opposing ends of one of the jaws is caused to enter into the opening disposed at the opposing end of opposing jaw. Moreover, in a further embodiment, the string applying assembly further comprises a tie advancing mechanism disposed within one of the jaws, adapted to advance the tail portion of the surgical string for entering into the opening disposed at an opposing end of opposing jaw.

In a further aspect, the present invention provides a surgical string applicator system for anastomosis surgery, which includes the surgical string applicator described above and an intra-lumenal position guide. The intra-lumenal position guide comprises a guide section having a distal end connected to a lead member, and a proximal end detachably connected to a proximal handle member. The guide section includes a cylindrical body and multiple parallel grooves disposed circumferentially therearound. The intra-lumenal position guide can be placed into a tubular organ first, and the zip-ties can be fastened by the surgical string applicator around the guide section. The guide section can be cut by a surgical blade, and can also be perforated longitudinally by a circular stapler, which assists central alignment of two divided segments of a tubular organ.

In yet a further aspect, the present invention provides a method of anastomosis surgery using surgical strings. In one embodiment, the method comprises fastening a first and a second zip-ties circumferentially around a tubular organ or a connecting region between two tubular organs, with the first and second zip-ties beside each other with a space therebetween sufficient for dissecting the tubular organ or the connecting region by a cutting edge; dissecting the tubular organ or the connecting region at the space between the first and second zip-ties, forming a first tubular portion with a first zip-tied end and a second tubular portion with a second zip-tied end; resecting a target segment from the second tubular portion, forming a resected end; placing one head member of a circular stapling device through resected end into the second tubular portion with a locking shaft of the one head member protruding from the resected end, and centrally fastening the resected end around the locking shaft of the one head member to form a centrally fastened resected end; placing another head member of the circular stapling device into the first tubular portion against the first zip-tied end, with a locking shaft of the another head member protruding from the first zip-tied end adjacent to the first zip-tie; joining the locking shafts and pulling the head members of the circular stapling device together with the first zip-tied end and centrally fastened resected end against each other; stapling the first tubular portion and the second tubular portion together, with staples encircling the first zip-tied end and the centrally fastened resected end; and cutting tissues encircled by the staples and removing cut tissues and the zip-tie to recreate a tubular path.

In a specific embodiment, the present invention is directed to a method of colorectal anastomosis surgery using surgical strings such as zip-ties. The method comprises fastening a first and a second zip-ties circumferentially around rectum or sigmoid colon, with the first and second zip-ties beside each other with a space therebetween sufficient for insertion of a cutting edge; dissecting at the space between the first and second zip-ties, forming dissected rectum with a first zip-tied end and dissected colon with a second zip-tied end; resecting a target segment from the dissected colon, forming a resected end; placing one head member of the circular stapling device through the resected end into the colon with a locking shaft of the one head member protruding from the resected end, and centrally fastening the resected end around the locking shaft of the one head member to form a centrally fastened resected end; placing another head member of a circular stapling device into the dissected rectum against the first zip-tied end, with a locking shaft of the another head member protruding from the first zip-tied end adjacent to the first zip-tie; joining the locking shafts and pulling the head members of the circular stapling device together with the first zip-tied end and the centrally fastened resected end against each other; stapling the rectum and the colon together, with staples encircling the first zip-tied end and the centrally fastened resected end; and cutting tissues encircled by the staples and removing cut tissues and the zip-tie to recreate a colorectal path.

The advantages of the present invention will become apparent from the following description taken in conjunction with the accompanying drawings showing exemplary embodiments of the invention.

BRIEF DESCRIPTION OF THE DRAWINGS

FIG. 4 shows a circular stapler for colorectal anastomosis surgery. FIG. 4A shows the anvil and the head of the circular stapler joined through the anvil shaft and the center rod of the head.

FIGS. 13 and 13A show a zip-tie in another embodiment of the present invention in open and closed positions, respectively, wherein the inner surface of the zip-tie includes a plurality of protuberances at the head portion and the gear rack is disposed on the outer surface.

FIG. 28 is a perspective view of a surgical string applicator in a further embodiment of the present invention.

FIG. 29 is a side view of a surgical string applicator in another embodiment of the present invention, in which the curved jaws have an elliptical shape when they are closed, suitable for insertion into a cannula, or trocar used in laparoscopic surgery. FIG. 29A is a partial side view of the surgical string applicator shown in FIG. 29, with one of the curved jaws opened. FIG. 29B is a partial side view of a surgical string applicator in a further embodiment of the present invention, showing distally hinged jaws in a completely open position.

It is noted that in the drawings like numerals refer to like components.

DETAILED DESCRIPTION OF THE INVENTION

In one embodiment, the present invention provides a method of anastomosis surgery using zip-ties.

For the purpose of understanding and appreciating the differences of the method of the present invention from, and the advantages over, the prior art methods, the existing stapled and sutured colorectal anastomosis surgery methods are briefly described first in reference to drawings.

Figure 1:
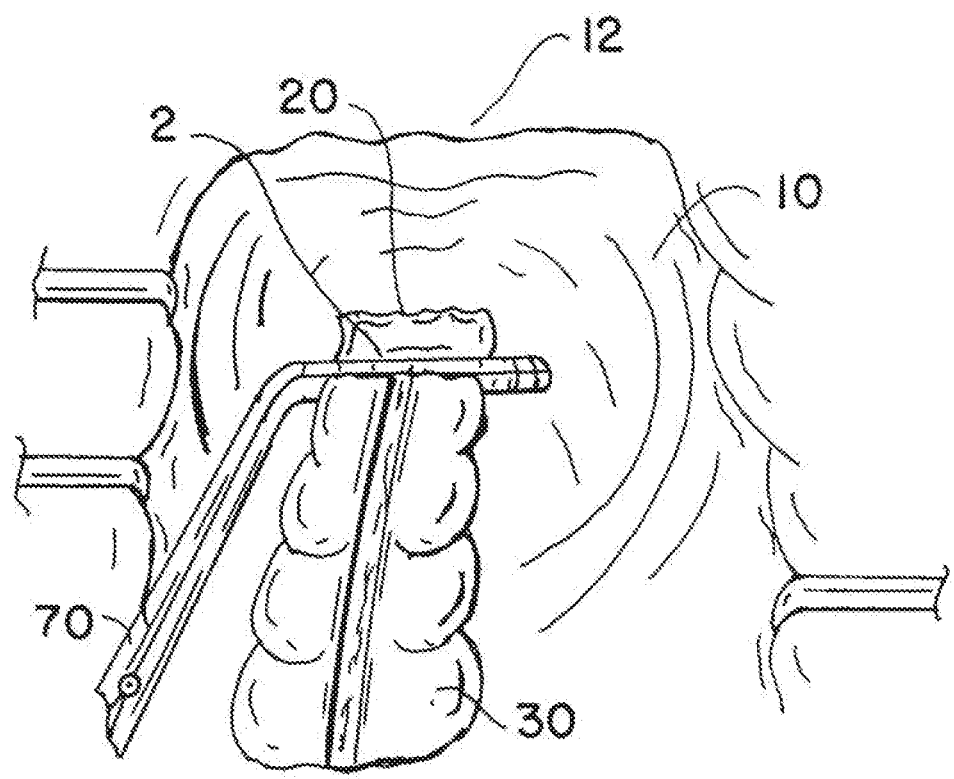
FIG. 1 illustrates the rectosigmoid region of a patient exposed in an open colorectal anastomosis surgery, with a clamp next to the dissecting site on the lower part of the rectum prior to anastomosis.

FIG. 1 illustrates the rectosigmoid region of a patient exposed in an open colorectal anastomosis surgery, with a clamp 70 clamping immediately next to the dissecting site 2 between the rectum 20 and the colon 30 in the lower pelvis cavity 10 behind the pubis 12.

Figure 2:
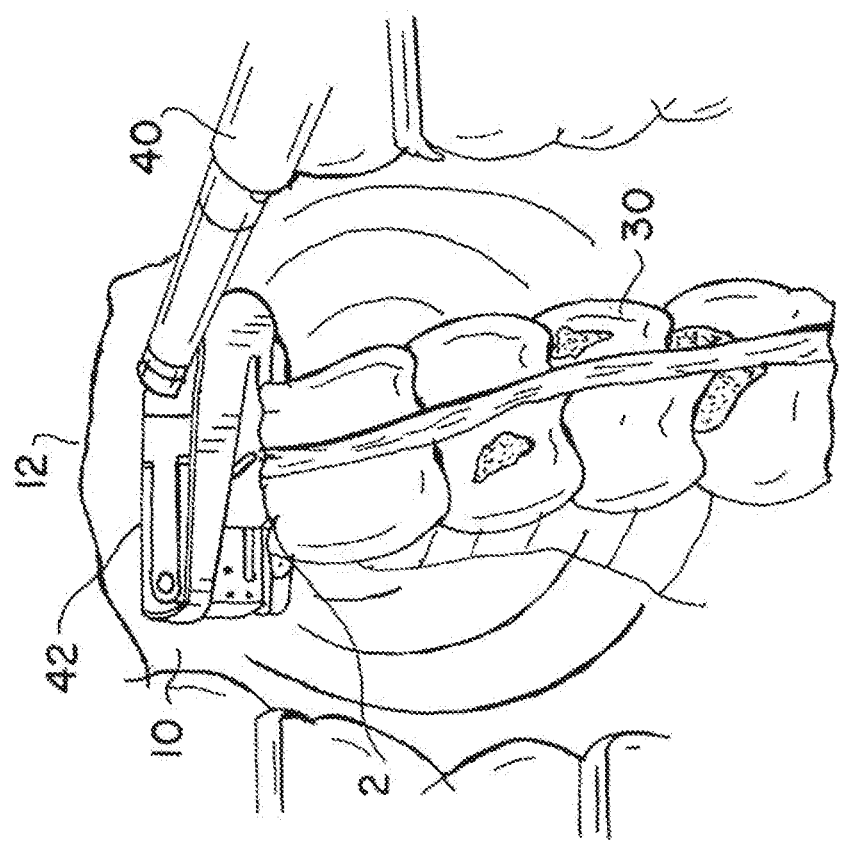
FIG. 2 illustrates transecting the rectum using a linear cutting stapler in a double or a triple stapling open rectosigmoid resection surgery.

In a double or a triple stapling open rectosigmoid resection procedure, a linear stapler 40 is used to close the rectum 20 and the colon 30 at the dissecting site 2, as shown in FIG. 2. The linear stapler has a head 42 which includes a disposable cartridge carrying staples. When the linear stapler is activated, it staples the tissue with two double rows of staples with a space therebetween. The dissecting site 2 is then transected in the space between the two double rows of staples. This can be performed manually by the surgeon using the superior edge of the staples as a guide. Alternatively, the dissecting site 2 can be mechanically transected using a linear cutting stapler that has a linear blade disposed between the two rows of staples. When the linear cutting stapler is activated, it staples the tissue with two parallel rows of staples first, and then dissects the tissue by the blade in the space between the two rows of the staples.

Figure 3:
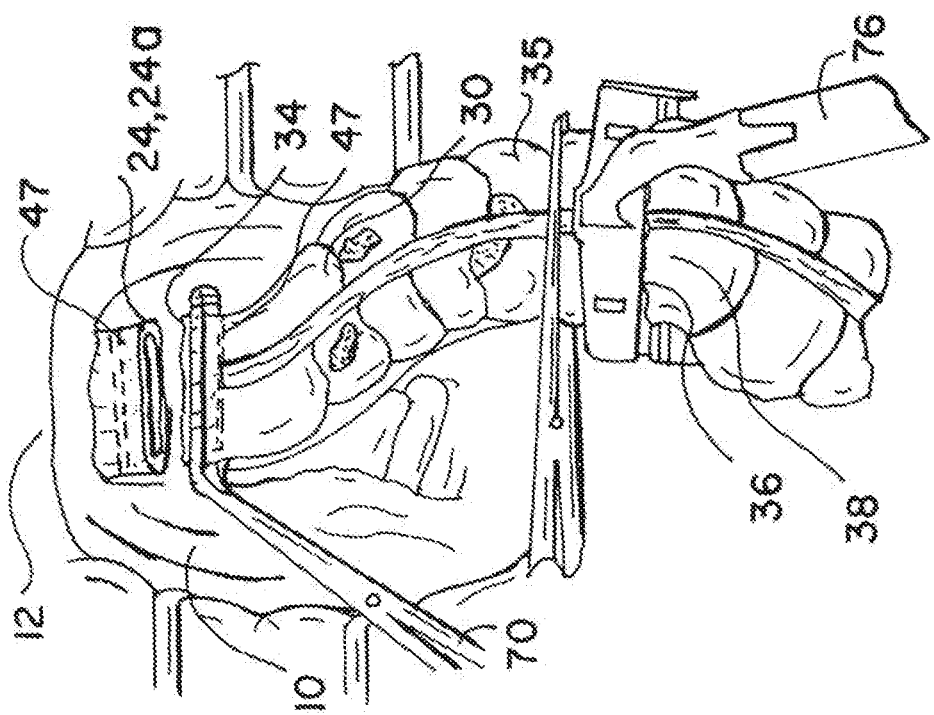
FIG. 3 illustrates resection of a target segment in the colon using a linear cutter.

As shown in FIG. 3, the dissection results in two free dissected ends, one dissected end 24 is a stapled linear closure 24a of the rectum 20, and the other dissected end 34 is a stapled linear closure of the colon 30. As further shown in FIG. 3, subsequently a target segment 35 in the colon 30, which may include a tumor or other abnormalities, is resected at a resecting site 36 by a linear cutter 76, which results in a resected end 38.

To rejoin the rectum and the colon after resection, a circular stapler is used. FIG. 4 illustrates a circular stapler 50 known in the art. Circular stapler 50 includes an elongated shank 52 with a handle 51 on one end and a cartridge 54 on the opposing end. As shown in FIG. 4A, cartridge 54 carries a plurality of staples arranged in a circle at the front end 58 of the cartridge. Extending forward from cartridge 54 is a center rod 56, which is herein also referred to as a locking shaft, adapted to interlock with an anvil shaft 66 (another locking shaft) of a removable anvil 60. When center rod 56 is interlocked with anvil shaft 66, anvil 60 can be pulled toward cartridge 54 until the surface 62 of anvil 60 against the front end 58 of cartridge 54. Since anvil 60 and cartridge 54 are two head members of a circular stapling device, and herein they are also referred to as one head member and another head member or vise versa.

Figure 5:
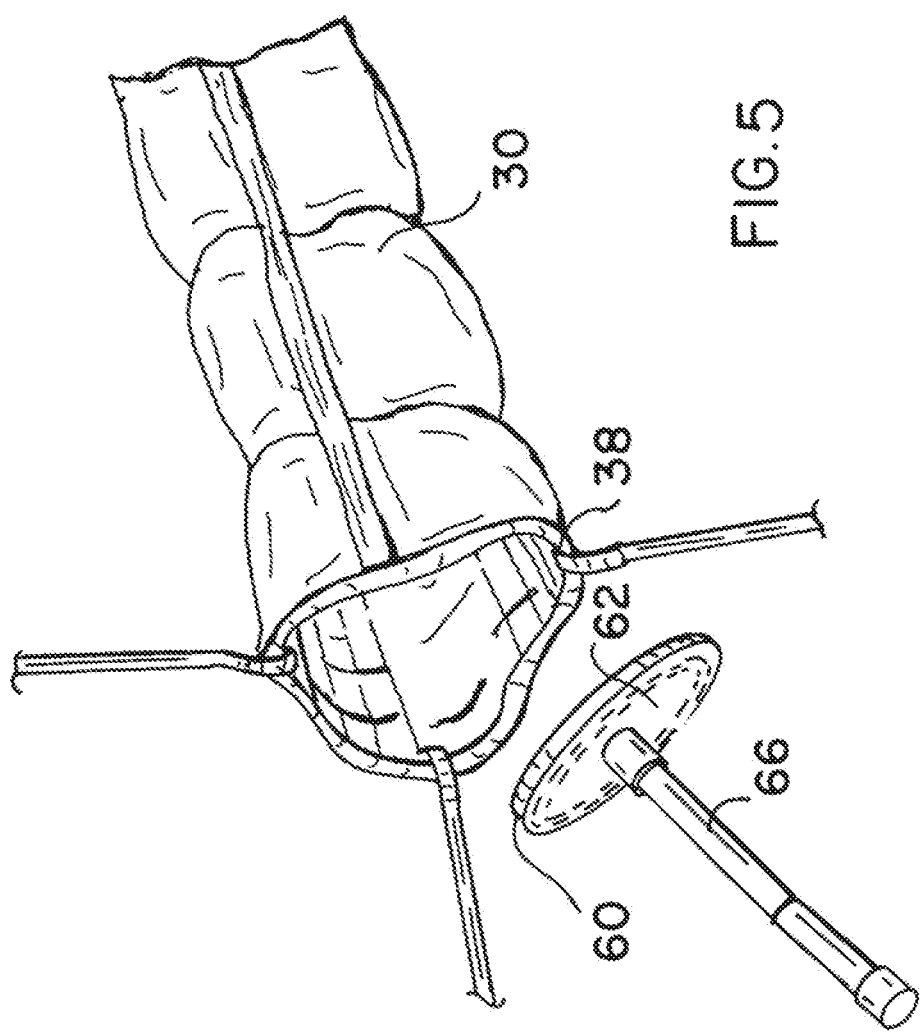
FIG. 5 illustrates after resection of the target segment, the anvil of the circular stapler is placed into the open proximal colon in a double or a triple stapling rectosigmoid resection surgery.
Figure 6:
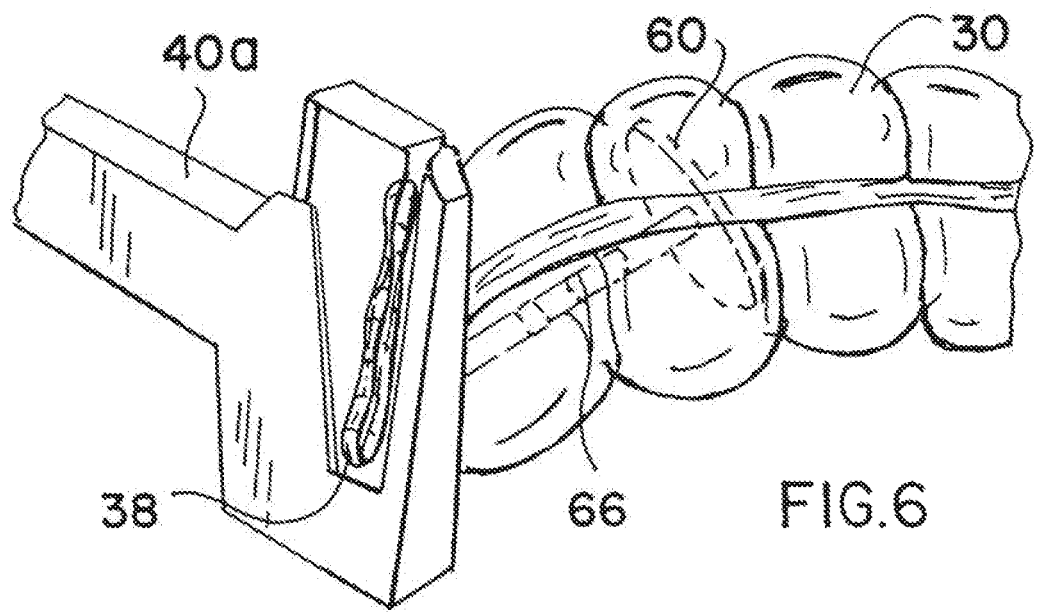
FIG. 6 illustrates the proximal colon containing the anvil is closed with a linear stapler.
Figure 6A:
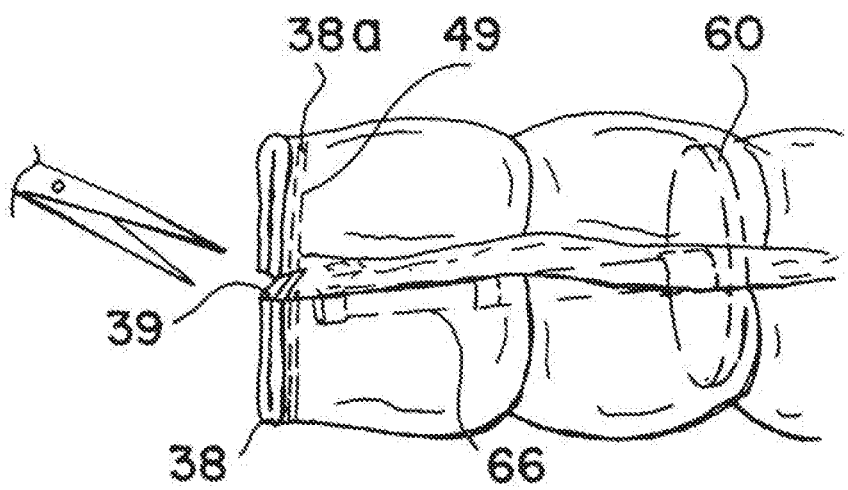
FIG. 6A illustrates a small incision is made at the midpoint of the stapled linear closure to retrieve the anvil shaft for a triple stapled procedure.

As illustrated in FIG. 5, to rejoin the rectum and the colon using circular stapler 50, anvil 60 is placed into the lumen of the colon 30 from the resected end 38. In the triple stapling colorectal anastomosis procedure, the resected end 38 is closed by a linear stapler 40a, which forms a linear closure 38a fastened by staples 49 as shown in FIGS. 6 and 6A. Anvil shaft 66 is pulled out from the stapled linear closure 38a through a small incision 39 at about the midpoint of the linear closure. Alternatively, in a double stapling colorectal anastomosis procedure, the resected end 38 is sutured onto anvil shaft 66 (see FIG. 9).

Figure 7:
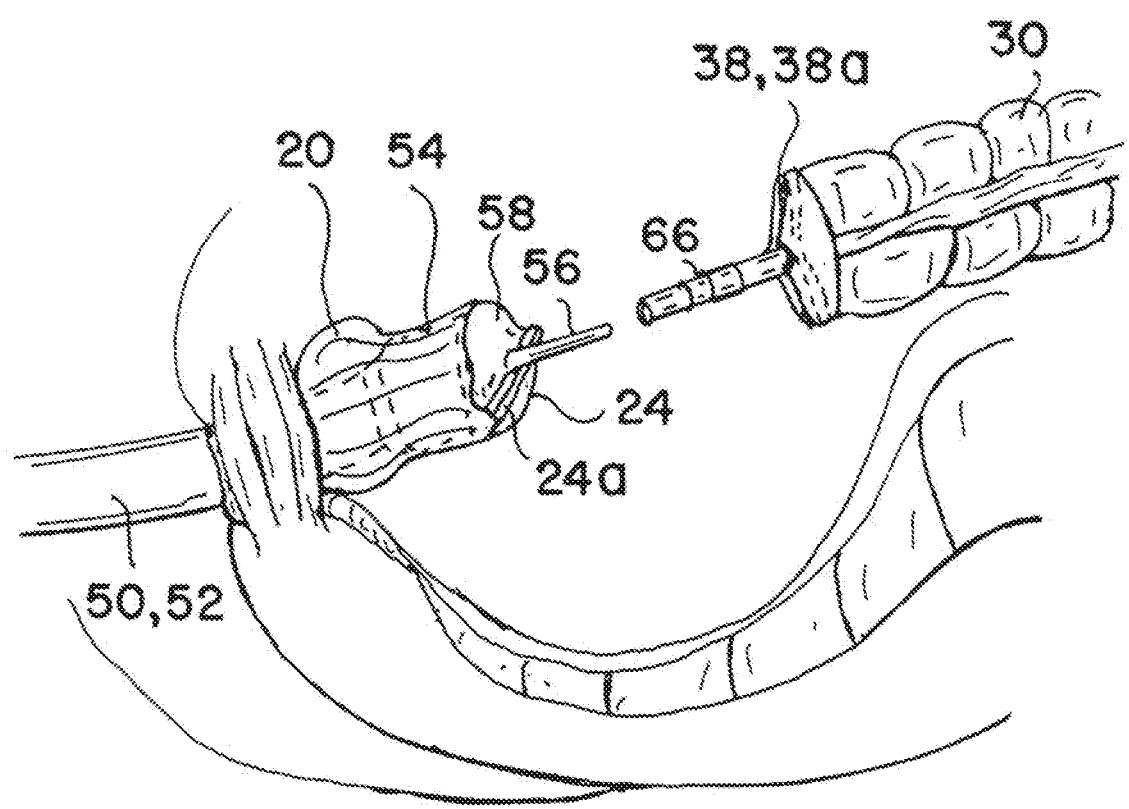
FIG. 7 illustrates that the head of the circular stapler is transanally placed into the rectum, and the tip of the center rod is advanced to perforate the rectal linear staple line at its midpoint.
Figure 8:
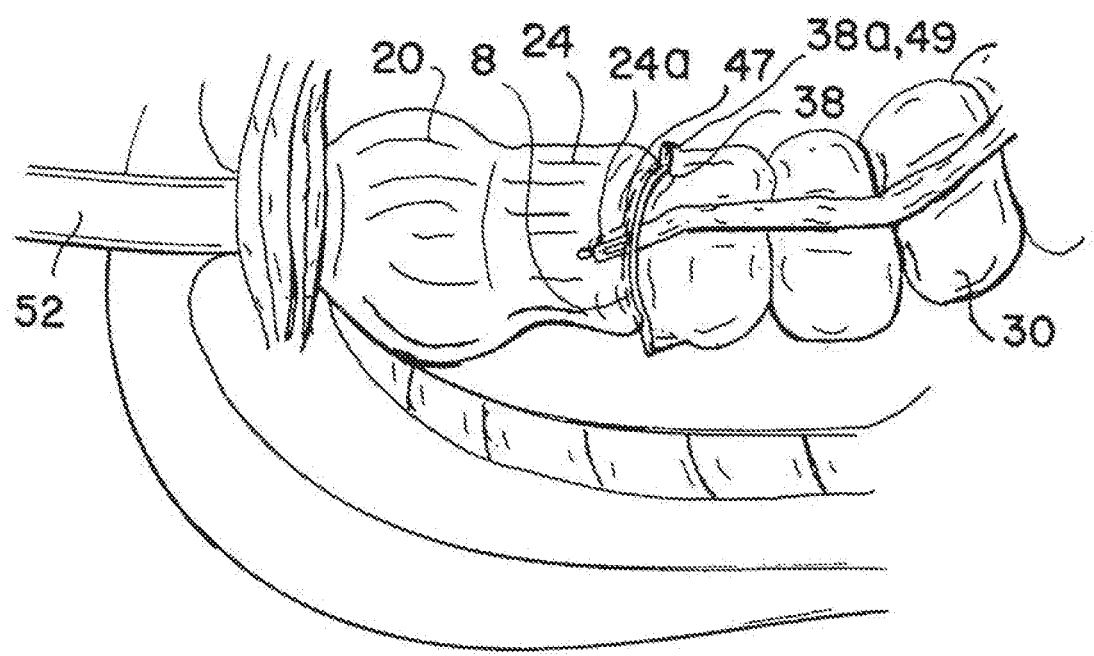
FIG. 8 illustrates that the anvil is closed against the stapling and cutting cartridge of the circular stapler. The colon is positioned so that the two linear staple lines are at right angles to one another in a cross-like mode.

On the other hand, as shown in FIG. 7, the cartridge 54 is transanally inserted into the rectum 20 and advanced to the extent that the front end 58 of cartridge 54 is positioned against the stapled linear closure 24a, and then center rod 56 is advanced to perforate the linear staple line about its midpoint. Center rod 56 and anvil shaft 66 are engaged and interlocked through a locking mechanism within (not shown). Then, anvil 60 is pulled toward the cartridge 54, along with the colon 30, until surface 62 of anvil 60 is against the front end 58 of cartridge 54, as shown in FIG. 8. As shown, the stapled linear closure 24a of dissected end 24 is horizontal, and the colon 30 is positioned to have the stapled linear closure 38a of resected end 38 in a vertical orientation, so that the two linear staple lines are at right angles to one another. The circular stapler 50 is activated to fasten dissected end 24 and resected end 38 together by placing a circular double staggered row of anastomosing staples, which results in a stapled circular closure 8 between the rectum 20 and the colon 30. Then, a circular blade disposed within cartridge 54 cuts through the colon and the rectum inside the double rows of staples, and the cartridge 54 is transanally removed together with anvil 60 and the cut tissues, which results in the recreated colorectal pathway, see FIG. 8A.

Figure 8A:
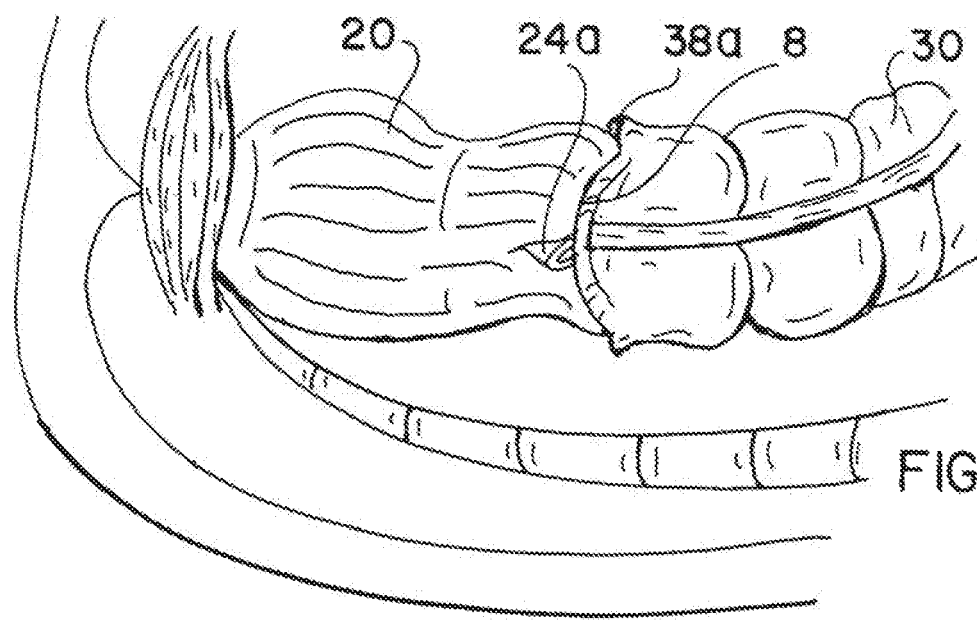
FIG. 8A illustrates the interface region between the rectum and the colon after the circular stapler is transanally retrieved, showing the overlap between the two stapled linear closures and stapled circular closure resulted from a triple stapling rectosigmoid resection procedure.

As shown in FIGS. 8 and 8A, in the triple stapling colorectal anastomosis procedure, the stapled circular closure 8 formed in the final step overlaps with the stapled linear closures 24a and the stapled linear closure 38a. The overlapped areas have higher risks of leakage and the tissues in the overlapped areas tend to scar, which may ultimately lead to stricture of the recreated pathway.

Figure 9:
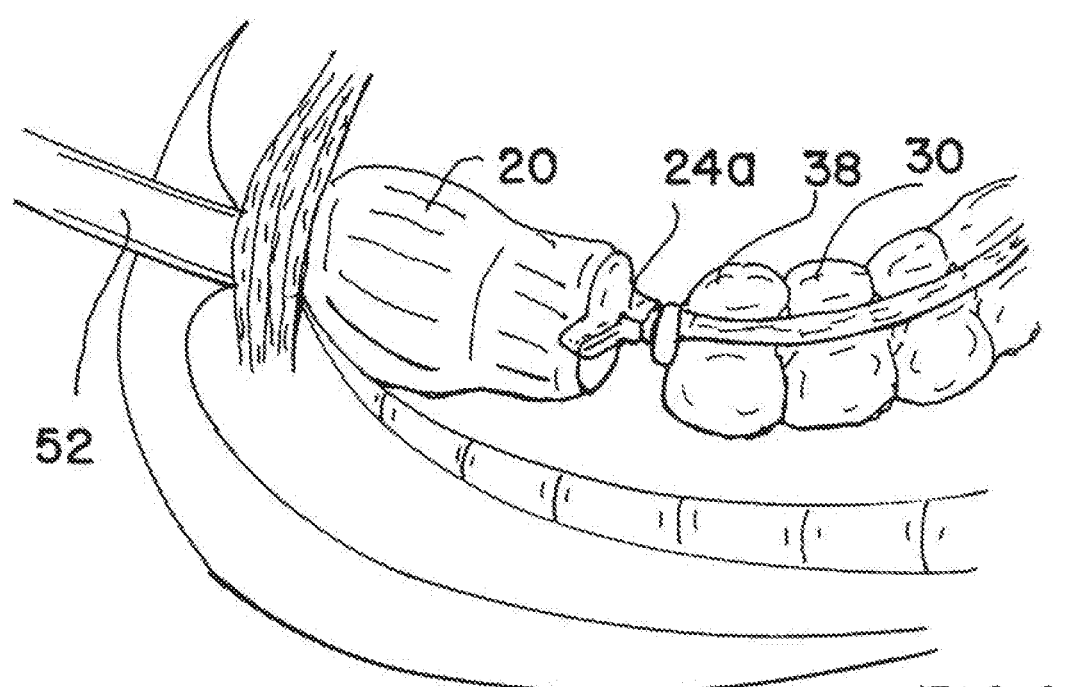
FIG. 9 illustrates the stapled linear closure of the rectum and sutured closure of the colon during a double stapling rectosigmoid resection procedure, when the anvil shaft and center rod of the circular stapler are joined, prior to the anvil being closed against the cartridge of the head.

FIG. 9 illustrates the stapled linear closure of the rectum and sutured closure of the colon during a double stapling rectosigmoid resection procedure, when the anvil shaft and center rod of the circular stapler are joined, prior to the anvil being closed against the cartridge of the head. As shown, in this procedure the resected end 38 is sutured onto anvil shaft 66, therefore, there is no stapled linear closure at the resected end 38. However, in the subsequent step of circular stapling, the stapled circular closure formed still overlaps with the stapled linear closure 24a. Therefore, the same issues discussed above in the triple stapling colorectal anastomosis procedure are present.

Figure 10:
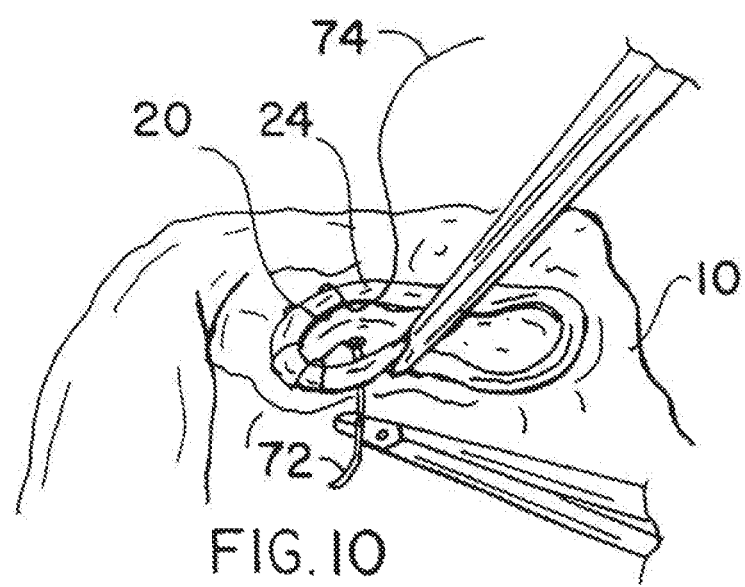
FIG. 10 illustrates manual suturing of the dissected end of the rectum stump to apply a traditional open manual pursebelt.

In an open rectosigmoid resection procedure using manual suture without linear staplers, the colon 30 is dissected from the rectum 20 at the dissecting site 2 as shown in FIG. 1, by a linear cutter (not shown). The dissected end 24 is manually sutured by the surgeon using needle 72 and suture belt 74 to close the rectal stump, as illustrated in FIG. 10. After resection of a target segment in the colon, a circular stapler is used to rejoin the rectum and the colon as described above. In this procedure, the resected end 38 is sutured onto anvil shaft 66, as described above in the double stapling rectosigmoid resection procedure. The cartridge 54 of circular stapler 50 is transanally placed into the rectum 20, and then the rectum 20 and the colon 30 are rejoined by circular stapling, as described above. In the manual sewn procedure, no stapled linear closure is present and hence the overlaps between the stapled linear closure and the stapled circular closure are avoided. However, as can be appreciated from FIG. 10, when the dissecting site 2 is located in the lower extreme of the pelvis cavity behind the pubis 12, manually suturing the dissected end 24 can be very difficult, and sometimes, it can be impossible. Due to poor accessibility, quality of suturing can be poor, which increases the risks of leakage and surgical complications.

The present invention overcomes the problems of existing surgical procedures by providing a method of zip-tying or zip-tied anastomosis surgery, which can be used for anastomosis surgery of various tubular organs, including the connection region between two tubular organs.

In one embodiment, the method is a double zip-tied procedure, which comprises the following steps:

(a) fastening a first and a second zip-ties circumferentially around a tubular organ or a connecting region between two tubular organs, with the first and second zip-ties beside each other with a space therebetween sufficient for dissecting the tubular organ or the connecting region by a cutting edge;

(b) dissecting the tubular organ or the connecting region at the space between the first and second zip-ties, forming a first tubular portion with a first zip-tied end and a second tubular portion with a second zip-tied end;

(c) resecting a target segment from the second tubular portion, forming a resected end;

(d) placing one head member of a circular stapling device through resected end into the second tubular portion with a locking shaft of the one head member protruding from the resected end, and centrally fastening the resected end around the locking shaft of the one head member to form a centrally fastened resected end;

(e) placing another head member of the circular stapling device into the first tubular portion against the first zip-tied end, with a locking shaft of the another head member protruding from the first zip-tied end adjacent to the first zip-tie;

(f) joining the locking shafts and pulling the head members of the circular stapling device together with the first zip-tied end and centrally fastened resected end against each other;

(g) stapling the first tubular portion and the second tubular portion together, with staples encircling the first zip-tied end and the centrally fastened resected end; and (h) cutting tissues encircled by the staples and removing cut tissues and the zip-tie to recreate a tubular path.

In a further embodiment, in step (f) fastening the resected end around the locking shaft of one head member is achieved by fastening a third zip-tie circumferentially around the resected end onto the locking shaft of one head member of the circular stapling device. As can be appreciated, this provides a triple zip-tied procedure.

Alternatively, centrally fastening the resected end around the locking shaft of the one head member is achieved by manually suturing the resected end around the locking shaft of the one head member of the circular stapling device.

Herein, the term "tubular organ" includes, but is not limited to, arteries, veins, esophagus, bile ducts, small intestine, colon, sigmoid colon, rectum, ureter, urethra, fallopian tube, and appendix. It should be understood that the first tubular portion and the second tubular portion resulted from the dissection can belong to the same tubular organ, or belong to two different tubular organs, depending on the location of the target segment and purpose of the surgery. For example, in a situation of a colon cancer patient with a tumor located in a middle portion of the colon, the first tubular portion and the second tubular portion are both a part of the colon, and the recreated tubular path is within the colon itself. However, in another situation of a colon cancer patient with the tumor located in the sigmoid colon, which is directly connected to the rectum, if the dissecting site 2 shown in FIG. 1 is at an upper portion of the rectum, the first tubular portion can be the rectum stump, and after resecting sigmoid colon, the remaining second tubular portion is the colon. Therefore, the recreated tubular path is between the rectum and the colon. In some extreme situations, small intestine may be connected to the rectum after resecting the colon.

Herein, the phrase "dissecting a tubular organ or a connecting region between two tubular organs" refers to, in most cases, transecting the tubular organ or the connecting region, which cuts the tubular organ in transverse to its longitudinal axis. However, "dissecting a tubular organ or a connecting region between two tubular organs" herein also includes cutting the tubular organ in an angle deviating from the transverse direction, which, sometimes, is required in an anastomosis procedure. Surgically, this action has also been referred to as dividing two tubular portions.

The term "target segment" refers to a segment of the tubular organ, or the connecting portion of two tubular organs, which is to be resected by the anastomosis surgery. Typically, the target segment includes abnormal tissue or abnormal organ structures affected by clinical conditions such as benign and malignant neoplasias of the digestive tract, unspecific inflammatory diseases of digestive tract such as ulcerative colitis and Crohn's disease, appendicitis, Meckel's diverticulitis, esophagus diverticulitis, Barrett's disease, obesity with metabolic disturbances, esophagus hernia, bile tract lithiasis, ureter stricture, and urethra stricture. In colorectal anastomosis surgery, the target segment typically include abnormal tissue or abnormal organ structures affected by conditions such as benign and malignant colorectal neoplasias, diverticular disease, megacolon, volvulus, ulcerative colitis, Crohn's disease, colorectal trauma, colorectal or pelvic endometriosis, Ischemic colitis, and anorectal abscess. However, the target segment may be normal tissue and organ structure. For example, in surgical treatment of functional diseases, modifying the bowel movement and producing chronic constipation, such as in treatment of colic inertia, a selected normal segment of the digestive tract needs to be resected.

Herein, the term "centrally fastening" refers to fastening the tubular organ toward the center of the longitudinal axis of the tubular organ. In contrast, a linear stapler fastens a tubular organ linearly in substantially transverse direction of the longitudinal axis of the tubular organ. The term "cutting edge" includes regular surgical blades, and a sharp edge, blade, or knife carried in surgical cutting devices.

Figure 11:
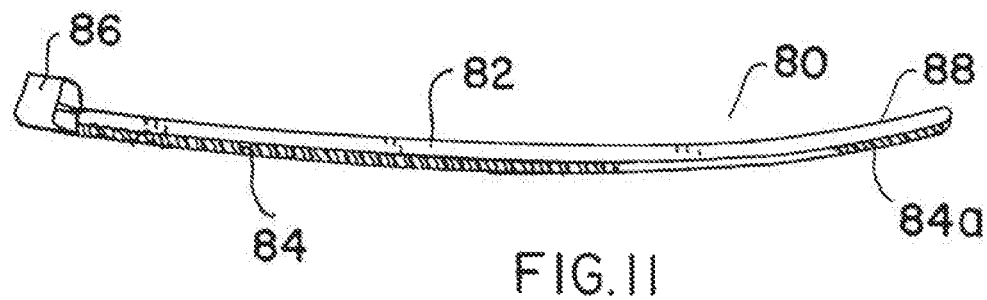
FIGS. 11 and 11A show a zip-tie in one embodiment of the present invention in open and closed positions, wherein the gear rack is disposed on the inner surface of the zip-tie.
Figure 11A:
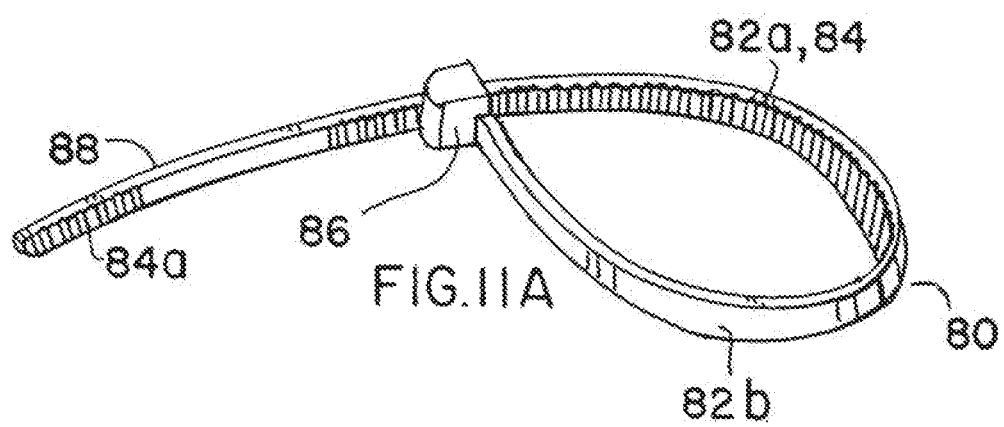

FIGS. 11 and 11A show a zip-tie 80 in one embodiment of the present invention, in an open and a closed configuration, respectively. Structures and mechanisms of zip-ties are known in the art. In general, a zip-tie, also commonly called cable tie, has a head, an elongated strap body or belt portion, and a tail. As shown in one embodiment, zip-tie 80 includes a sturdy belt 82 with an integrated gear rack 84 on one surface of the belt, a head 86 on one end and a tail 88 on the opposing end. Head 86 is in a form of a small open case including a passage and a ratchet (not shown) disposed within the passage. Once the belt with the gear rack has been pulled through case 86 and past the ratchet, it is prevented from being pulled backward, and the resulting loop can only be pulled tighter in one direction. The dimensions of belt 82 may vary depending on the type of anastomosis surgery or the diameter of the tubular organ. For example, for colorectal anastomosis surgery, belt 82 may have a length from about 5 cm to about 10 cm, a width from about 2 mm to about 5 mm, and a thickness from about 1 mm to about 4 mm. However, for artery anastomosis surgery, belt 82 may have a substantially shorter length.

Figure 12:
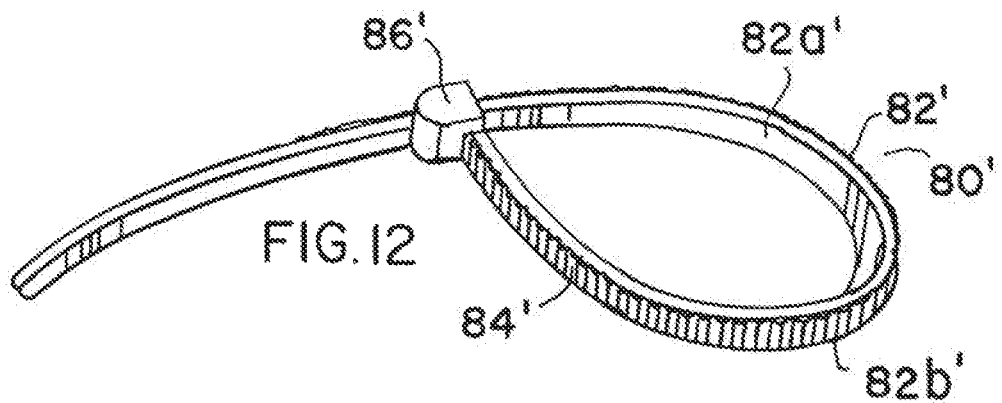
FIG. 12 shows a zip-tie in a further embodiment of the present invention in a closed position, wherein the inner surface of the zip-tie is smooth and the gear rack is disposed on the outer surface.

As shown in FIG. 11A, the gear rack 84 is disposed on the inner surface 82a of belt 82, defined in reference to the locked loop. The gear rack may serve two functions. One function is a locking mechanism of the zip-tie as described above. Another function is to provide a textured surface inside the loop, which provides a certain level of friction or resistance between the tissue and the zip-tie to prevent potential sliding of the zip-tie when it is applied onto the tissue. In an alternative embodiment, zip-tie 80' has the gear rack 84' integrated on the outer surface 82'b of belt 82', as shown in FIG. 12. In zip-tie 80', head or case 86' includes a ratchet (not shown) adapted to lock the gear rack on the outer side of the loop. In this embodiment, the inner surface 82a' of the loop is smooth, which is suitable for more fragile tissue type.

FIG. 13 shows a zip-tie 90 in a further embodiment. As shown, zip-tie 90 has gear rack 94 integrated on the outer surface 92b of belt 92. Moreover, belt 92 also includes multiple protuberances or ridges 98 on the inner surface 92a of belt 92 to provide a certain level of friction or resistance between the tissue and the zip-tie. In the embodiment shown, the protuberances are in a triangular-like shape, however, protuberances or ridges can have various suitable shapes and configurations. Alternatively, the inner surface 92 can have textured surface, such as grooves, indentations, pores, or surface roughness.

In all embodiments described above, the tail of the zip-tie may also have a surface texture such as ribs, teeth, gear rack and grooves in the direction transverse to the longitudinal axis of the zip-tie. The surface texture provides means for mechanical gripping when an automated applicator is used. In one embodiment, the tail of the zip-tie may optionally include a gear rack 84a as shown in FIGS. 11 and 11A. In one configuration, this tail gear rack is the same as the gear rack 84 and disposed on the same side as the gear rack 84 provided at the belt portion, and with this configuration the tail portion can be locked into the head with the same mechanism used in the belt portion. In another configuration, the tail gear rack can be on either side of the tail, for engagement with gripping mechanism of zip-tie applicator as described hereinafter.

The zip-tie can be made of biocompatible materials, suitable for surgical use, and can be produced by plastic molding or other suitable methods known in the art. In one embodiment, the entire zip-tie including the case and the belt is made of one material. In another embodiment, the inner side and the outer side of the belt are made of two different materials. For example, the outer side is made of a more sturdy material to support the gear rack, and the inner side is made of a resilient material with surface roughness or textures. The two different sides can be joined together by heat, surgical adhesives, or other suitable materials or methods to form an integral belt. Suitable materials for making the zip-tie includes, but are not limited to, synthetic polymers, such as nylon, silicone, and other suitable surgical plastics.

The zip-tie can be either fastened circumferentially around the tubular organ manually, or mechanically using a zip-tie applicator in a laparotomy or laparoscopic procedure, or in a natural orifice procedure, such as insertion through the mouth, anus, vagina, urethra, or other natural orifice.

Figure 14:
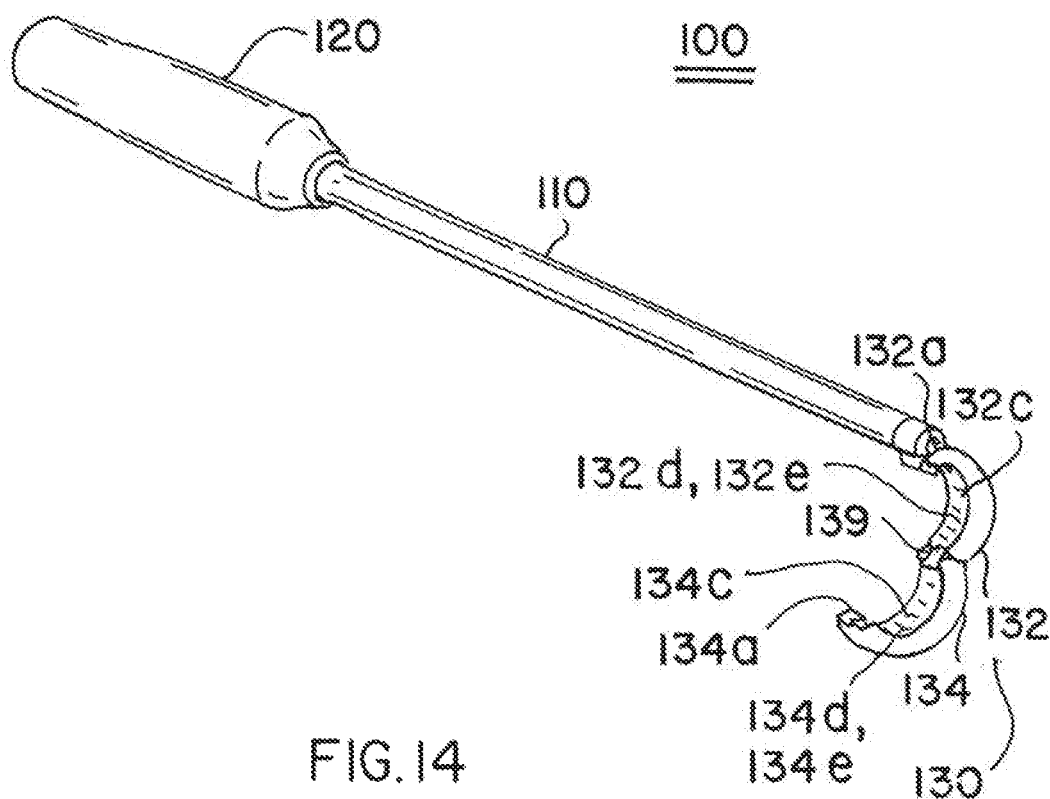
FIG. 14 shows an illustrative perspective view of a zip-tie applicator in one embodiment of the present invention.

FIG. 14 illustrates a zip-tie applicator in one embodiment of the present invention. As shown, zip-tie applicator 100 includes an elongated shaft 110, a handle 120 connected to shaft 110 on one end, and a zip-tie tensioner 130 connected to shaft 110 on the opposing end. In the embodiment shown, zip-tie tensioner 130 includes two semi-circular members, or curved jaws 132 and 134 connected to each other by a hinge 139. The open end 134a of semi-circular member 134 can be attached to the fixed end 132a of semi-circular member 132, which forms a circular closure. The plane of semi-circular members 132 and 134 is at about 90 degree angle from the longitudinal axis of elongated shaft 110. On the interior side 132c of semi-circular member 132, there are two parallel grooves 132d and 132e, which are continued by parallel grooves 134d and 134e on the interior side 134c of semi-circular member 134. There is a distance between grooves 132d and 132e, as well as between 134d and 134e, sufficient for insertion of a cutting edge for dissecting tissue between two fastened zip-ties. When in use, two zip-ties are placed into the grooves, one in grooves 132d and 134d, and one in grooves 132e and 134e. When semi-circular member 134 is closed, a tensioning or fastening mechanism (not shown) disposed within the semi-circular members fastens the zip-ties, with a tubular organ tightened within. It is noted that various zip-tie tensioning mechanisms are known in the art, and can be used for zip-tie applicator of the present invention. Preferably, the tensioning mechanism is operated by a motor disposed with one of the semi-circular members. Furthermore, preferably, the zip-tie applicator further includes a belt cutting blade disposed within one of the semi-circular members, which is adapted to cut the belt after the zip-tie is fastened. Moreover, handle 120 can further include a control mechanism which is connected to zip-tie tensioner 130 through shaft 110. In a further embodiment, the zip-tie applicator can further include two semi-circular blades (not shown) disposed in semi-circular members 132 and 134 between grooves 132d and 132e, and grooves 134d and 134e respectively. When two zip-ties are fastened as described above, the two blades can be activated by the motor to dissect the tubular organ fastened by the zip-ties. In the embodiment shown in FIGS. 14 and 14A, the curved jaws 132 and 134 are transverse to the elongated shaft 110, and in an alternative embodiment the curved jaws are aligned with the elongated shaft. The structure and mechanism of the zip-tie applicator are further described later after the description of the zip-tied anastomosis surgery method.

Figure 15:
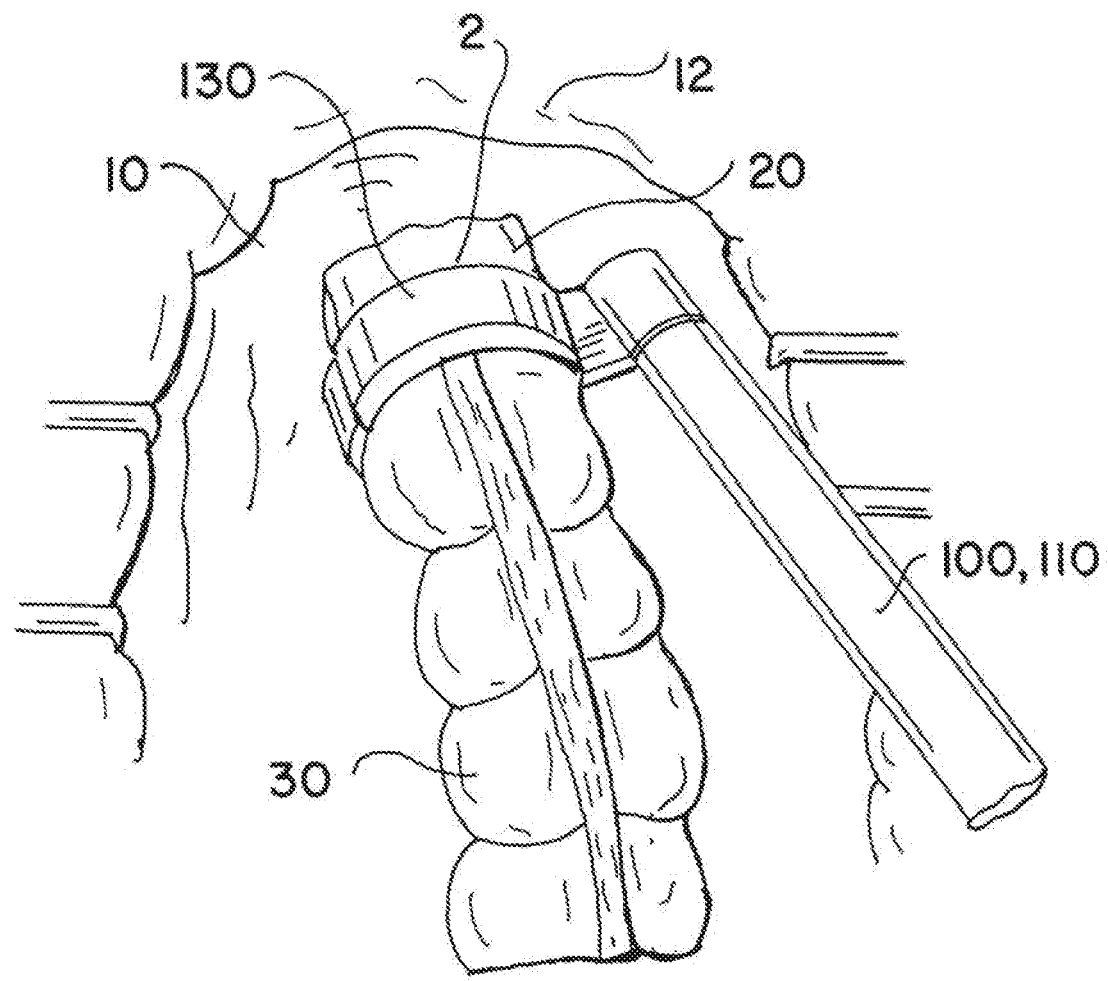
FIG. 15 illustrates the use of the zip-tie applicator shown in FIG. 14 in an open rectosigmoid resection procedure, with the zip-tie tensioner of the applicator wrapping around the rectum at the dissecting site to fasten the rectum circumferentially using two zip-ties carried within the tensioner.
Figure 16:
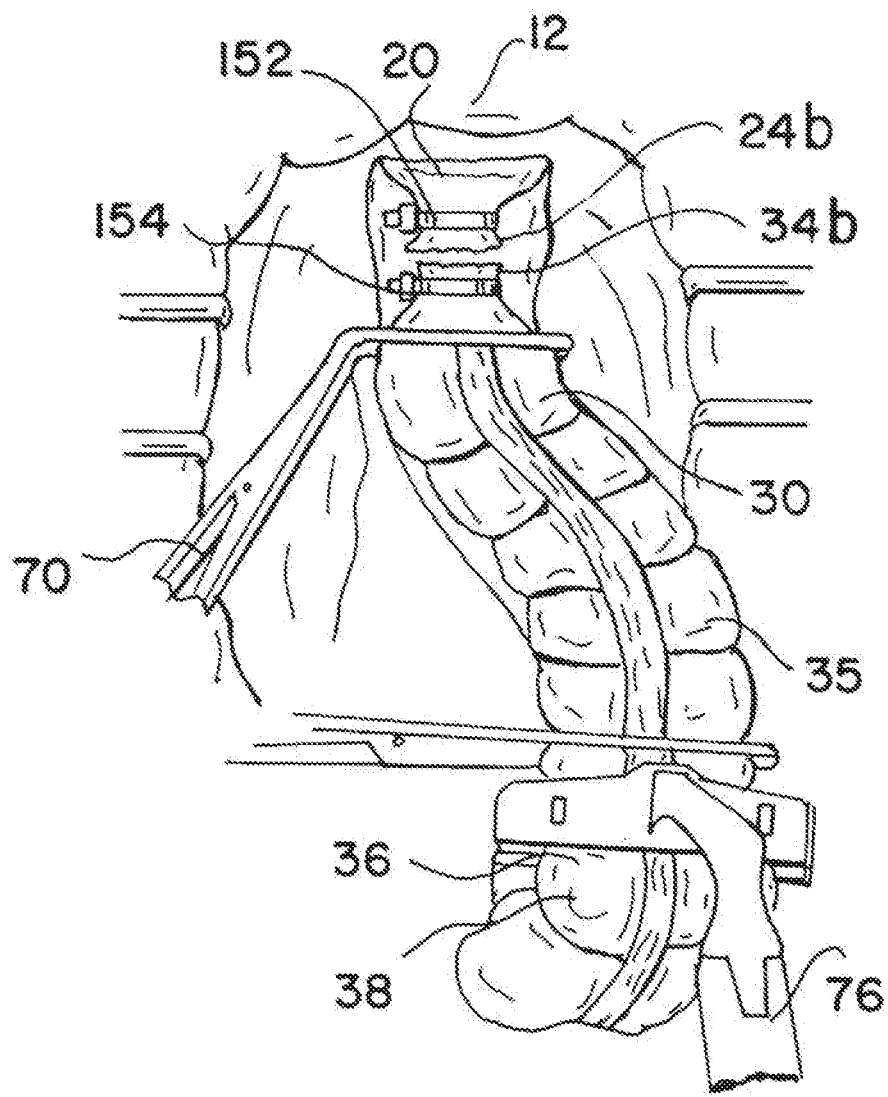
FIG. 16 illustrates two zip-tied ends after transecting the rectum, and resection of a target segment in the colon.

FIG. 15 thru 18 illustrate an example of the zip-tied anastomosis surgery method of the present invention, using zip-tie applicator 100 in an open rectosigmoid resection surgery. As illustrated in FIGS. 15 and 16, in an open rectosigmoid resection surgery, after the rectosigmoid region is exposed following the existing surgical procedure, semi-circular members 132 and 134 of zip-tie tensioner 130 of zip-tie applicator 100 is placed around the rectum 20 at a selected dissecting site 2. Zip-tie tensioner 130 carries two zip-ties therein. Zip-tie applicator 100 is activated using a control mechanism on the handle to fasten two zip-ties circumferentially around the rectum 20 in parallel. Then, zip-tie applicator is triggered again to dissect the rectum 20 in the space between the two fastened zip-ties 152 and 154 using the blades carried with the semi-circular members. Alternatively, zip-tie applicator 100 is removed after fastening the zip-ties, and the rectum 20 is manually dissected in the space between the two fastened zip-ties 152 and 154 by the surgeon. As shown in FIG. 16, this results in two zip-tied dissecting ends, one zip-tied end 24b is a zip-tied closure of the rectum stump, and the other zip-tied end 34b is a zip-tied closure of the colon 30. As further shown in FIG. 16, subsequently the target segment 35 in the colon 30 is resected at a resecting site 36, either by a linear cutter 76 or other surgical blades, which results in a free resected end 38.

After resection, the rectum 20 and the colon 30 are rejoined using an existing circular stapler. It is noted that for the purpose of the present invention, various commercially available circular staplers, such as DST circular staplers manufactured by Covidien (Norwalk, Conn.), CDH circular staplers manufactured by ETHICON ENDO-SURGERY (Cincinnati, Ohio), and the circular staplers manufactured by Power Medical Interventions (Langhorne, Pa.) can be used.

Figure 20:
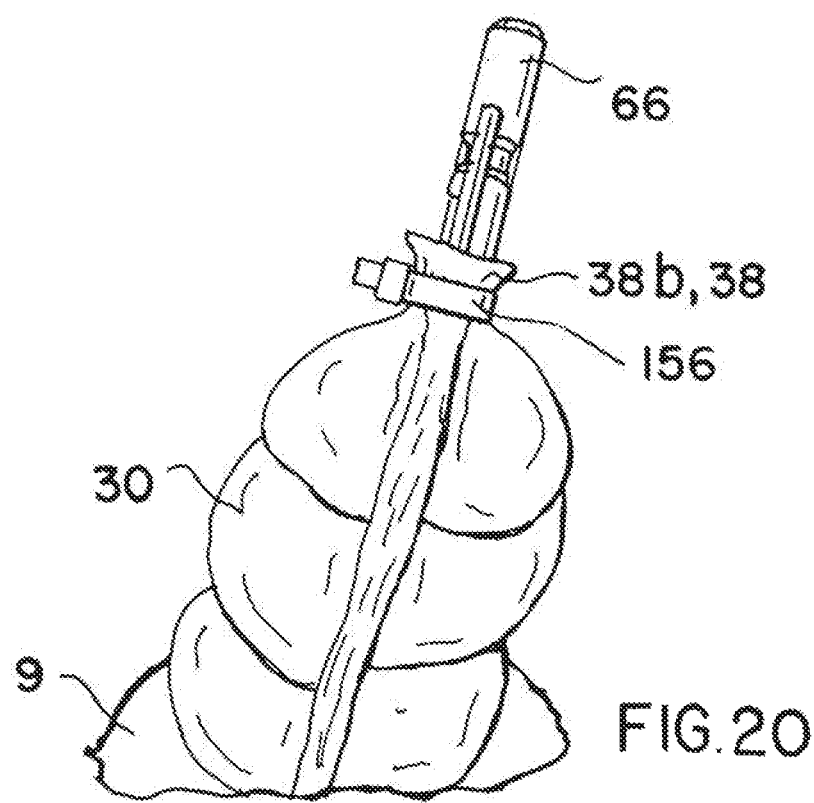
FIG. 20 illustrates the zip-tied resected end of the colon with the anvil placed with the proximal colon and the anvil shaft remaining outside of the colon, prior to placing the colon back into the pelvis cavity.

As illustrated in FIG. 5, anvil 60 is placed into the lumen of the colon 30 from the resected end 38 with anvil shaft 66 remaining outside of resected end 38. Then, the resected end 38 is centrally fastened. Preferably, a third zip-tie 156 is fastened circumferentially around resected end 38, which fastens the colon 30 onto anvil shaft 66 to form a zip-tied resected end 38b, as shown in FIG. 20. The third zip-tie can be fastened either manually by the surgeon or using a zip-tie tensioner. This zip-tie tensioner may have the same or different structure from zip-tie tensioner 130 of zip-tie applicator 100. To fasten resected end 38 onto the anvil shaft only one zip-tie is needed. Moreover, the resected end 38 can be more readily accessed by the surgeon in either open surgery or laparoscopic surgery, therefore, the elongated shaft of zip-tie applicator 100 is not needed. Alternatively, resected end 38 can be tied around anvil shaft 66 by purse-belt suture. Using either the third zip-tie or purse-belt suture, the method forms a centralized closure.

Figure 17:
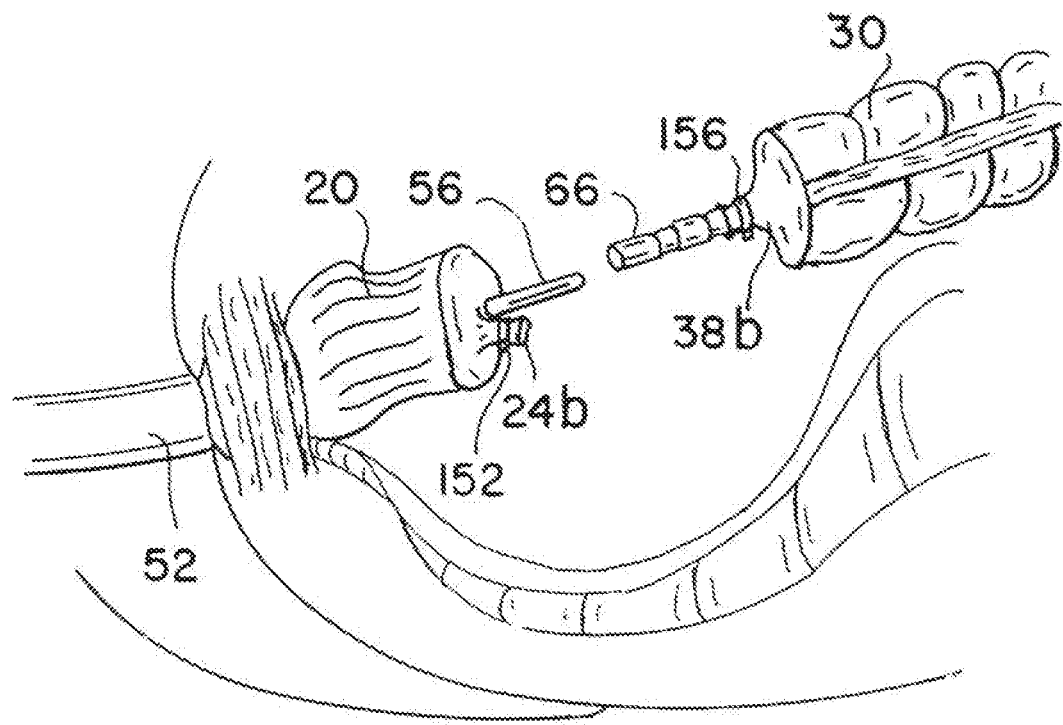
FIG. 17 illustrates that the head of the circular stapler carrying the stapling and cutting cartridge is transanally inserted into the rectum, and the tip of the center rod is advanced to perforate zip-tied closure adjacent to the zip-tie.

Then, cartridge 54 of circular stapler 50 carrying stapling and cutting cartridge 58 is transanally inserted in the rectum 20 and advanced to the extent that cartridge 58 is positioned against the zip-tied end 24b, and then center rod 56 is advanced to perforate the zip-tied closure adjacent to the zip-tie, as shown in FIG. 17 (cartridge 54 is within the rectum 20 in FIG. 17). The point of perforation should be sufficiently close to the zip-tie, which is at the center of the zip-tied closure, so long as the zip-tie does not interfere with the connection between the center rod and the anvil shaft. To position the center rod adjacent to the zip-tie assures the zip-tied end to be enclosed within the circle of the staples.

Figure 17A:
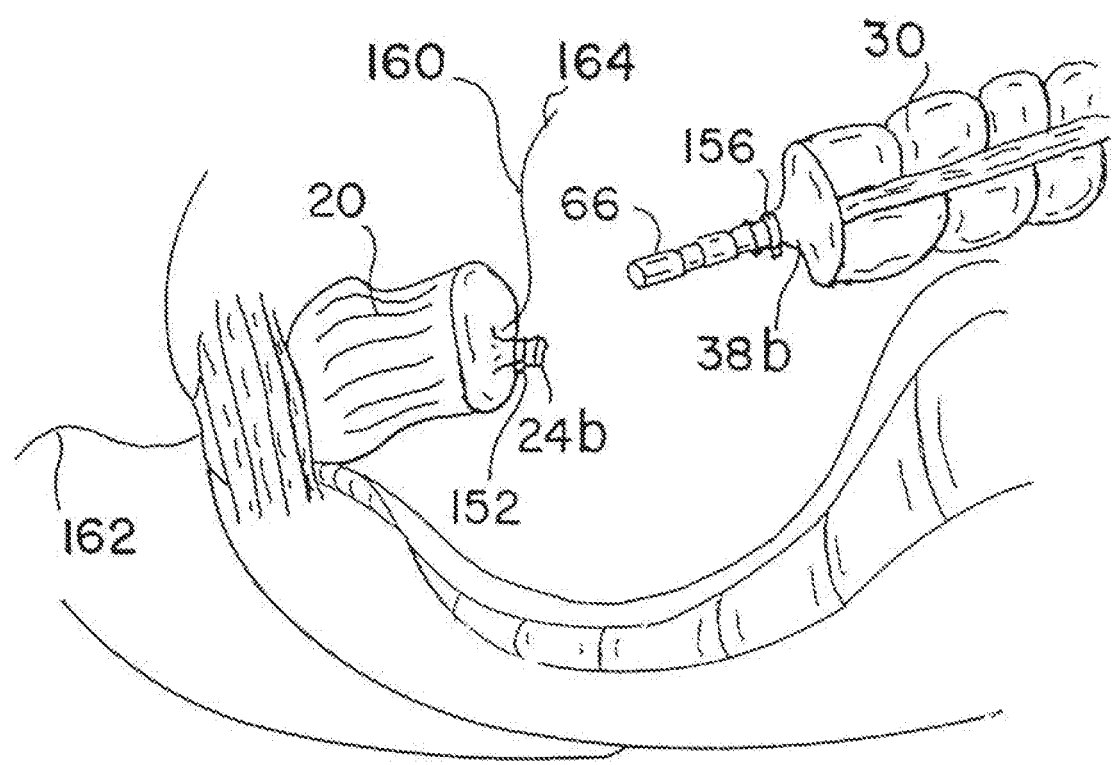
FIG. 17A illustrates that a guide wire is introduced into the rectum first with the distal end thereof remaining outside of the anus and the proximal end thereof in the abdomen cavity, before the distal end of the guide wire is fastened to the center rod of the circular stapler for guiding the center rod to perforate the zip-tied closure adjacent to the zip tie.

Optionally, an intraluminal guide wire can also be used to guide the center rod for perforation adjacent to the zip-tie. In rectosigmoid resection surgery, either laparotomic or laparoscopic procedure, sometimes it is difficult for the surgeon to see the position of the fastened closure of the rectum stump when advancing the center rod. To assure that the center rod perforates adjacent to the zip-tie, an intraluminal guide wire can be first introduced into the zip-tied rectum stump. The guide wire can be introduced from the abdomen cavity or through the anus. In one embodiment, as shown in FIG. 17A, a guide wire 160 is introduced from the abdomen cavity into the rectum by penetrating the distal end 162 of guide wire 160 through the zip-tied closure at a point adjacent to the zip-tie and the distal end 162 is taken out from the anus by the surgeon. Alternatively, the distal end 162 can also penetrate the zip-tied closure through the loop of the zip-tie. The distal end 162 is then fastened to center rod 56 of circular stapler 50. After the cartridge 54 of circular stapler 50 is inserted into the rectum 20 transanally, the center rod 56 is advanced in a direction guided by the guide wire 160. The guide wire 160 is pulled from its proximal end 164 by the surgeon, which assures that the center rod perforates the zip-tied closure adjacent to the zip-tie.

In another embodiment, the guide wire can be introduced transanally, which is particularly suitable for the situations of high colorectal anastomosis. In this embodiment, a flexible or rigid rectoscope can be inserted in the rectum through anus carrying guide wire 160 within. The proximal end 164 of guide wire 160 penetrates the zip-tied closure at a point adjacent to the zip-tie or through the loop of the zip-tie, and the proximal end 164 is pulled up from the abdomen cavity and the rectoscope is retrieved, with the distal end 162 remaining outside the anus, as shown in FIG. 17A. Then, the distal end 162 is fastened to center rod 56 of circular stapler 50. After the cartridge 54 of circular stapler 50 is inserted into the rectum 20 transanally, the center rod 56 is advanced in a direction guided by the guide wire 160, which perforates the zip-tied closure adjacent to the zip-tie. The guide wire is a flexible, thin wire made of metal, polymer, or other suitable surgical plastic materials. As can be appreciated from the above description, depending on the direction of penetration, either the distal end or the proximal end of the guide wire can be referred to as the first end or the second end.

Figure 18:
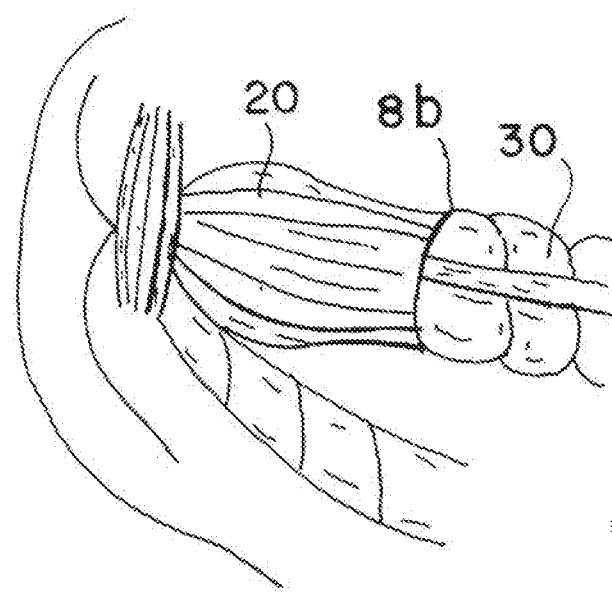
FIG. 18 illustrates the interface region between the rectum and the colon after the circular stapler is removed, showing a smooth circular closure between the rectum and the colon.

After center rod 56 is properly positioned, center rod 56 and anvil shaft 66 are engaged and interlocked through the locking mechanism between the center rod and the anvil shaft. Anvil 60 (within the colon 30) is pulled toward cartridge 54, along with the colon 30, until surface 62 of anvil 60 is against cartridge 58 (see FIG. 4A also). Then, circular stapler 50 is activated to staple the rectum 20 and the colon 30 together by placing a circular double staggered row of anastomosing staples, with the staples encircling zip-tied end 24b and zip-tied resected end 38b. This forms stapled circular closure 8b between the rectum 20 and the colon 30, as shown in FIG. 18. Then, the circular blade disposed within cartridge 54 cuts through the colon and the rectum inside the double rows of staples, and cartridge 54 is removed transanally together with anvil 60, the cut tissues and the zip-tie, which results in a smooth recreated colorectal pathway.

As shown in FIG. 18, using the zip-tied colorectal anastomosis procedure, the stapled circular closure 8b formed in the final step has a smooth interface between the rectum 20 and the colon 30. The areas of tissues being stapled are fresh and intact, absent any stitches or staples. Therefore, it substantially reduces the risks of leakage at the interface region and surgical complications. Since no overlap between different closures, such as those present in double and tripling stapling anastomosis procedures, the zip-tied colorectal anastomosis procedure has the advantages of less tissue scarring, and consequently less stricture of the recreated pathway.

As can be understood, this type of circular stapled interface can also be achieved using manual suturing procedure, where both the dissected end 24 of the rectum and the resected end 38 of the colon are manually sutured as shown in FIG. 10 and FIG. 9, respectively. However, as described earlier, manually suturing the dissected end 24 of the rectum is a very difficult process and often impossible to perform. Using the zip-tied colorectal anastomosis procedure of the present invention, the rectum can be readily fastened by zip-ties. Particularly, with the assistance of the zip-tie applicator, even the lower portion of the rectum can be readily fastened and dissected. This process has the advantage of shorter surgery time of the existing double or triple stapling anastomosis procedures, yet free of the inherent disadvantages of linear stapling methods.

The zip-tied anastomosis method can also be used in transabdominal end-to-end colorectal anastomosis procedure, which typically has the dissecting site at a higher portion of the rectum. In this surgical procedure, after initial dissection using double zip-ties as described above, the zip-tied dissected end 24 of the rectum can be reopened by cutting off the zip-tied portion, then anvil 60 of the circular stapler is placed into reopened dissected end 24 and the dissected end 24 is centrally fastened by a third zip-tie, with anvil shaft 66 staying outside. After resection of the target segment in the colon, the resected end 38 of the proximal colon is centrally fastened by a fourth zip-tie. An incision is made on the wall of the colon, and the cartridge 54 of the circular stapler is inserted into the colon through the incision, with the cartridge 58 placed against the zip-tied resected end, and the center rod 56 perforating the zip-tied closure adjacent to the zip-tie. Then, the center rod and the anvil shaft are joined and the anvil shaft is closed against the cartridge. The circular stapler is then activated to staple the rectum and the colon together, which forms stapled smooth circular closure, as described above. In this procedure, after cutting the tissues encircled inside the staples, the head together with the anvil, cut tissues and the zip-ties are removed from the incision on the wall of the colon, and the incision is closed by purse-belt suture.

Figure 19:
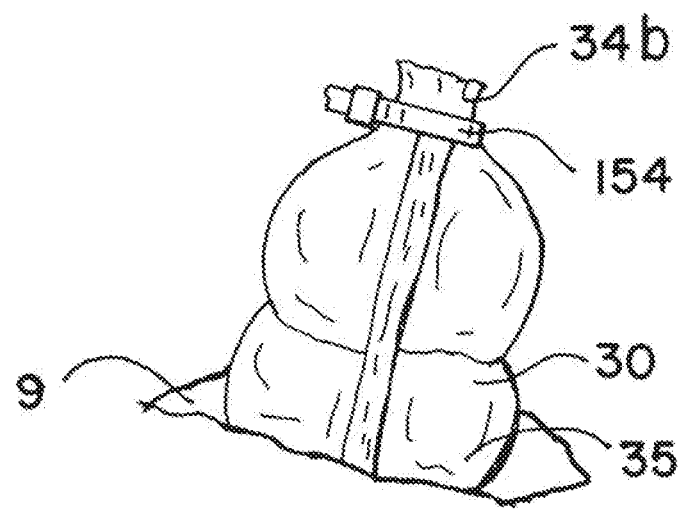
FIG. 19 illustrates the zip-tied transected end of the colon taken out from the small incision on the abdomen before resection of the target region.

Furthermore, the zip-tied anastomosis method can be used in laparoscopic surgery. In laparoscopic surgery within the abdominal or pelvic cavities, a small incision is made on the abdomen of a patient, and then a zip-tie applicator can be inserted into the pelvic cavity to dissect the colon from the rectum as described above in the open surgery, which is monitored using a laparoscope. After dissection, the zip-tied end 34b of the colon 30 is taken out from the pelvic cavity through the small incision 9, as shown in FIG. 19. Then, as described in the open surgery procedure, the target segment 35 is resected, which forms a resected end 38. The circular stapler 50 is used to rejoin the colon and the rectum. As shown in FIG. 20, anvil 60 is placed into the proximal colon, and resected end 38 is fastened by a third zip-tie 156 onto anvil shaft 66. Then, the zip-tied colon is placed back into the pelvis cavity through the small incision 9. As described previously in the open surgery and shown in FIG. 17, the cartridge 54 of the circular stapler 50 is inserted into the rectum 20 transanally, and placed against the zip-tied end 24b with the center rod 56 perforating the zip-tied closure adjacent to the zip-tie. Then, center rod 56 and anvil shaft 66 are joined, and the anvil is closed against the cartridge. The circular stapler is then activated to staple the rectum 20 and the colon 30 together, which forms stapled smooth circular closure, as described above. After cutting the tissues encircled inside the staples by the circular stapler, the head, together with the anvil, cut tissues and the zip-ties are removed from anus, which forms the recreated colorectal pathway. The small incision on the abdomen is then closed by purse-belt suture.

For laparoscopic zip-tied anastomosis surgery, the zip-tie applicator may have a different structure. The zip-tie tensioner may comprise two semi-circular members, with one end of both semi-circular members pivotally attached to the elongated shaft. The semi-circular members are adapted to open and close as controlled by the control mechanism on the handle. Moreover, the two semi-circular members may also connect to the elongated shaft by a second pivot, which enables the plane of the semi-circular members to be adjusted at a desired angle when the zip-tie tensioner is advanced inside the pelvis cavity to the dissecting site.

In a further aspect, the present invention provides surgical string applicators for applying one or more surgical strings or surgical ties around a subject tubular organ in the anastomosis method described above. Herein, the term "surgical string" or "surgical tie" refers to an elongated flexible element having a cross sectional shape of rectangular, square, oval, circular, semicircular, or other geometric configurations. Surgical strings can be made of biocompatible, surgical grade, plastic materials, silicon, fiber, other materials suitable for surgical use. Optionally, the surgical strings may include surface textures. Moreover, surgical strings may also include self-locking mechanism such as a zip-tie. Exemplary embodiments of surgical strings include, but not limited to, flat straps, zip-ties, and surgical sutures or threads. In the anastomosis method described above the process is illustrated with zip-ties, however, other surgical strings can also be used, particularly with assistance of the applicators. Therefore, the anastomosis method of the present invention is also referred to as a mechanically assisted string-tied anastomosis method.

Figure 14A:
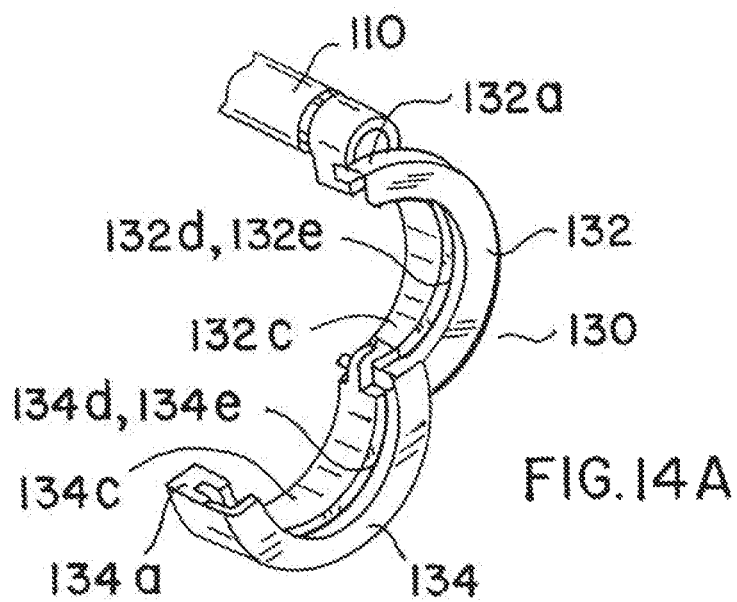
FIG. 14A shows an enlarged perspective view of the zip-tie tensioner of the applicator shown in FIG. 14.

FIGS. 21-29 illustrate several exemplary embodiments of surgical string applicators of the present invention, in addition to the embodiment shown in FIGS. 14 and 14A. When the surgical string applicator is design, or suitable, to apply zip-tie, it is also referred to as zip-tie applicator interchangeably.

Figure 21:
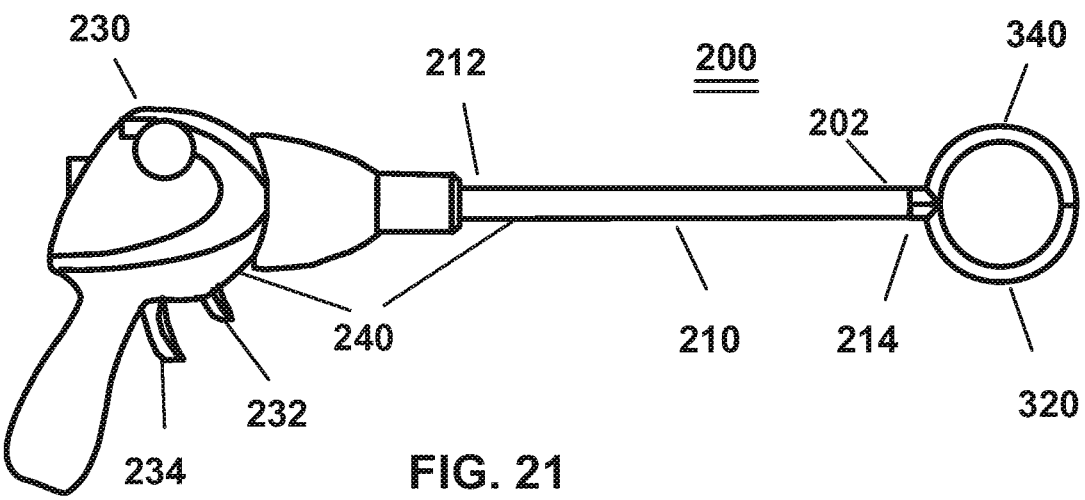
FIG. 21 is a side view of a surgical string applicator in one embodiment of the present invention.
Figure 21A:
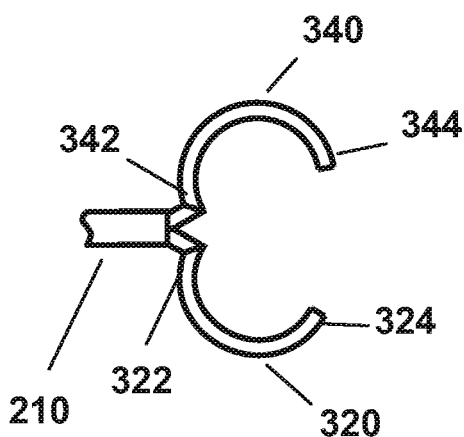
FIG. 21A is a side view of the surgical string applicator shown in FIG. 21, with the jaws opened.

FIGS. 21 and 21A show a surgical string applicator 200 in one embodiment of the present invention. As shown, surgical string applicator 200 includes an elongate hollow shaft 210, a handle portion 230 connected to proximal end 212 of shaft 210, and a string applying assembly that includes opposed first and second jaws 320, 340 connected to distal end 214 of shaft 210 and a string fastening mechanism adapted to engage and fasten one or more surgical strings such as zip-ties that will be placed within the jaws and will be applied to a tubular organ, as described hereinafter.

In surgical string applicator 200, each of jaws 320, 340 has a curved shape, generally semicircular, with the concave inner side facing the opposing jaw. The two curved jaws 320, 340 are aligned with each other, and are also aligned with elongated shaft 210, namely with the longitudinal axis of the jaws (from the proximal end 322, 342 to the distal end 324, 344) aligned with the longitudinal axis of shaft 210. The proximal ends 322 and 344 of the two jaws can be connected directly, or through an interface component, to the distal end 214 of shaft 210. At least one jaw can be pivotally moved relative to the opposing jaw, or both jaws can be pivotally moved relative to each other. Moreover, either jaw or both can be locked at a selected position. Furthermore, the pair of jaws can also be articulated relative to and rotated about the longitudinal axis of the elongated shaft, to facilitate positioning the jaws relative to a subject tubular organ. The rotation can be effected by either rotating the pair of jaws relative to the shaft, or by rotating the shaft itself. In the embodiment shown in FIG. 21A, both the first and the second jaws can be pivoted at their proximal ends. When jaws 320, 340 are closed, their distal ends 324 and 344 are against each other. As can be appreciated, when the curved jaws are opened, a tubular organ can be received through the opened distal ends 324 and 344, and then is captured or surrounded by jaws 320, 340 when the jaws are closed.

The dimensions of the jaws in surgical string applicator 200 can be determined according to particular surgery procedures where the device is used. For use in colorectal anastomosis surgery, typically the jaws may have a length (defined as the distance from the proximal end to the distal end at the outside of the jaws) from about 30 to about 80 millimeters (mm), and an outer cross-width (defined as the maximum distance between the outside of the two jaws in the direction transverse to the longitudinal axis of the jaws when the jaws are closed) preferably equal or less than the length. The jaws may have a width (transverse to the longitudinal direction of the jaw) from about 10 mm to about 30 mm, and a thickness (from the inner surface 326 to the outer surface 328 thereof, see FIG. 23A) from about 4 mm to about 12 mm, depending on the structural components in the jaw as described hereinafter. In one exemplary embodiment, the closed jaws have a length and an outer cross-width about 50 mm and an inner cross-width (defined as the maximum distance between the inside of the two jaws in the direction transverse to the longitudinal axis of the jaws when the jaws are closed) about 40 mm. The shaft typically has a diameter from about 8 mm to about 12 mm and the length can be from about 150 mm to about 350 mm, depending on the surgery procedure. As can be appreciated, for a tubular organ of smaller size, such as artery, the inner cross-width of the jaws can be smaller. Moreover, as described hereinafter, for laparoscopic surgery, the shape and dimension of the jaws can be different to meet the small incision requirement.

Figure 22:
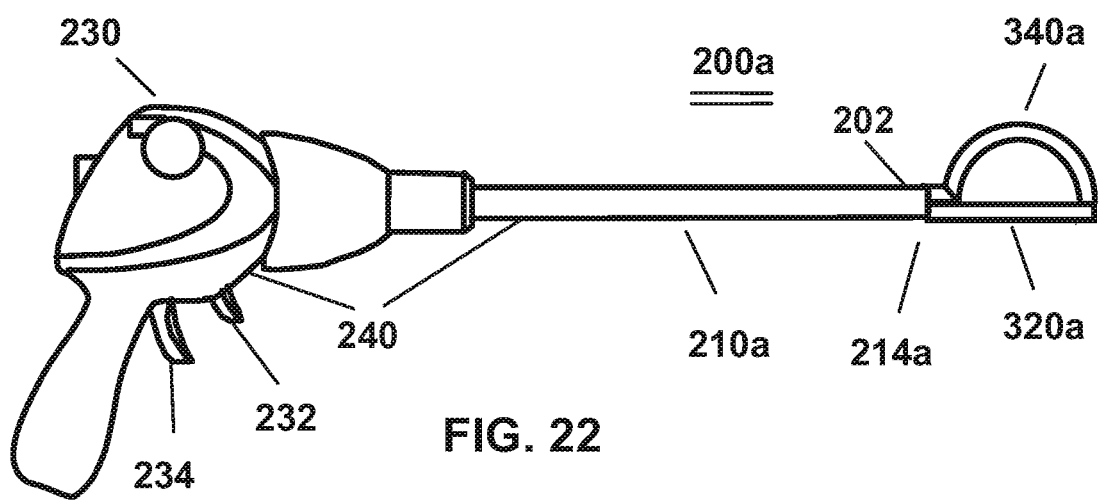
FIG. 22 is a side view of a surgical string applicator in a further embodiment of the present invention.
Figure 22A:
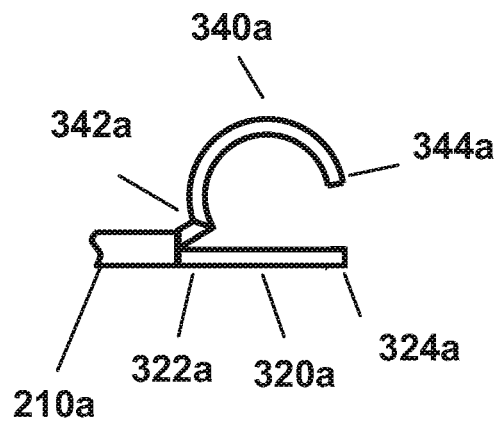
FIG. 22A is a side view of the surgical string applicator shown in FIG. 22, with one jaw opened.

FIGS. 22 and 22A show a surgical string applicator 200a in an alternative embodiment. As shown, surgical string applicator 200a includes a first straight jaw 320a and a second curved jaw 340a, both having the proximal ends 322a and 342a connected to distal end 214a of shaft 210a. As shown in FIG. 22A, in this embodiment the first jaw 320a is fixed, and the second curved jaw 340a pivots at its proximal end 342a to open and close the distal end 344a relative to the distal end 324a of the first jaw 320a. As can be appreciated, with this configuration the contact or mutual engagement between the two jaws is between the extreme distal end of the second jaw 340a and the inner side (the upper side in FIG. 22A) of the distal end of the first jaw 340a. The first and second jaws 320a, 340a can have the same length as jaws 320 and 340 of surgical string applicator 200 described above. However, the inner cross-width between the closed jaws 320a and 340a may be about half of that between jaws 320 and 340 described above, if jaw 320a has the same curvature as that of jaw 320. As can be appreciated, this configuration has a less dimension in the direction transverse to the longitudinal axis, which facilitates positioning of the jaws in limited spaces. Similar to that described in applicator 200, the pair of jaws in applicator 200a can also be articulated relative to and rotated about the longitudinal axis of the elongated shaft.

Figure 23:
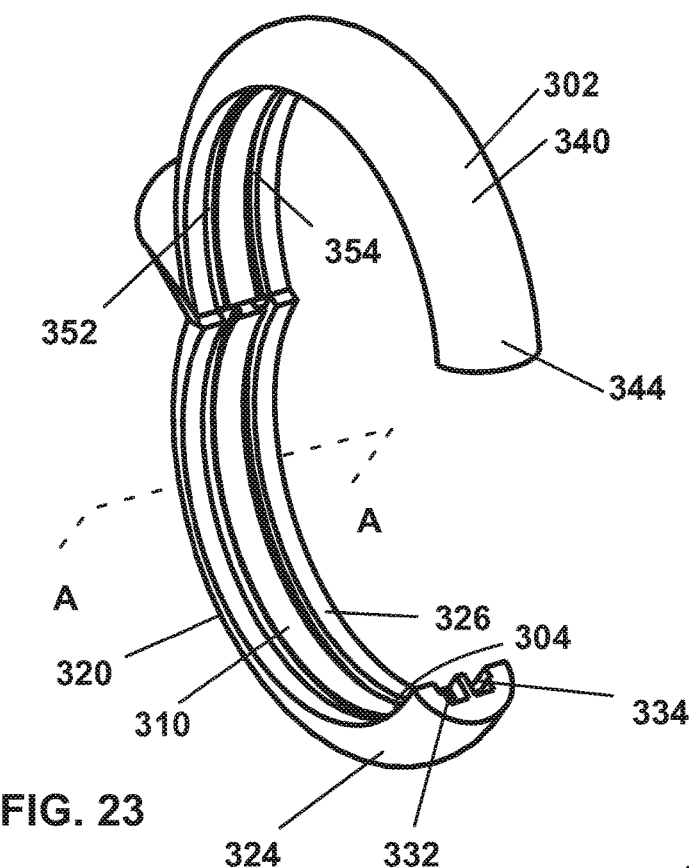
FIG. 23 is a front perspective view of the pair of jaws of the surgical string applicator shown in FIG. 21, with the jaws opened.
Figure 23A:
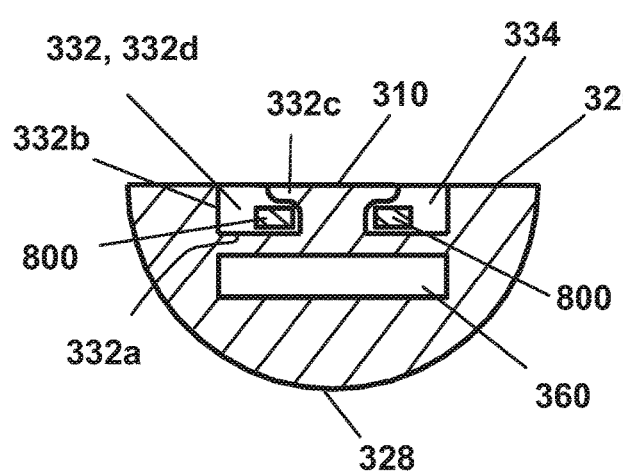
FIG. 23A shows a cross section of the lower jaw, along line A-A in FIG. 23, with two zip-ties placed within the grooves.

Further structures and operating mechanisms are now described using surgical string applicator 200, with exemplary structures adapted to apply zip-ties. Surgical string applicator 200a may have similar or different structures. In one embodiment, each of the two jaws 320 and 340 of surgical string applicator 200 has one or more grooves along the inner surface of the jaw. As shown in FIGS. 23 and 23A, first jaw 320 includes two parallel grooves 332 and 334 on inner surface 326 of the jaw, with a predetermined distance therebetween. The predetermined distance between grooves 332 and 334 corresponds to the distance between two zip-ties at the dissecting site for dividing the tubular organ by a blade. As such, this distance is also referred to herein as a cut-distance. Typically, the cut-distance can be from about 5 mm to about 20 mm, preferably from about 8 mm to about 16 mm; however, it may vary for different tubular organs.

Grooves 332 and 334 are recessed from and disposed linearly along inner surface 326. The width of each groove can be equal or greater than the width of a surgical zip-tie for receiving the zip-tie therein, with the planar surface of the zip-tie placed on the bottom of the groove. FIG. 23A shows a cross-section of the structure of grooves 332 and 334 in one exemplary embodiment shown in FIG. 23, with a zip-tie 800 placed therein. As shown, groove 332 has a channel-like structure, including a planar bottom 332a, a straight side wall 332b on one side, a protruding upper rim 332c on the other side, and a top opening 332d. The bottom 332a has a width substantially greater than the width of zip-tie 800, the zip-tie can be disposed underneath upper rim 332c in its resting stage. The top opening 332d has a width similar to or slightly greater than the width of the zip-tie. The upper rim 332c has a curved or inclined lower surface, facing the upper surface of the zip-tie. As such, when zip-tie 800 is pulled at its tail by the string fastening mechanism, the tensioning force causes the zip-tie sliding against the curved lower surface of the upper rim 332 upwardly and releases the zip-tie through top opening 332d. For holding a zip-tie within the groove, the upper rim can be continuous, or be present in separate segments, along the length of the groove.

In the embodiment shown, groove 334 has the same structure of groove 332, with a reversed orientation. However, groove 334 can also have the same orientation of groove 332. In either case, the distance between the two top openings is the cut-distance, and in the embodiment shown it corresponds to the width of ridge 310 between grooves 332 and 334.

Figure 23B:
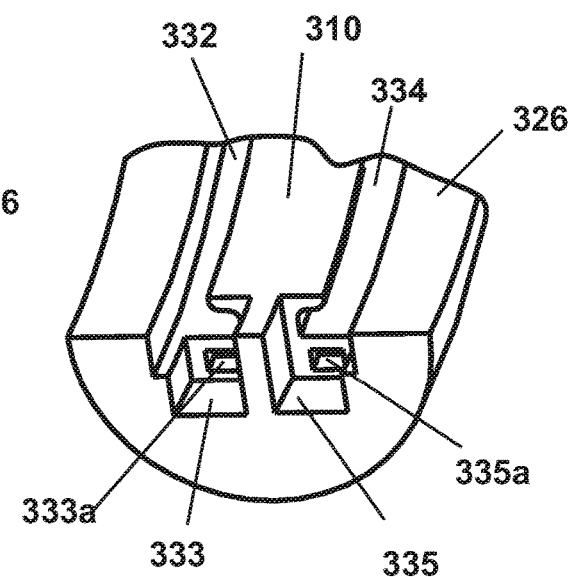
FIG. 23B is an enlarged view of the distal end of the lower jaw.

As further shown in FIG. 23B, distal end 324 of jaw 320 includes recesses 333 and 335, each at the distal end of one of the two grooves 332 and 334. Each recess extends below the bottom of the groove, which forms an alcove for receiving the head of one zip-tie, with the opening of the passage in the head facing the outmost end of jaw 320 toward the opposing jaw. Each recess has dimensions complimentary to the dimensions of the head of a zip-tie to be used. As further shown, each recess has a rear opening 333a or 335a on the proximal end of the recess underneath the corresponding groove 332, 334. The rear openings are used to receive the tail of a zip-tie after it passes through the head of the zip-tie. In one embodiment, the rear openings 333a and 335a are connected to a channel 360 underneath the grooves shown in FIG. 23A, which is used for one type of string fastening mechanism in an exemplary embodiment described hereinafter.

Similarly, second jaw 340 has two parallel grooves 352 and 354 that have the same structure of grooves 332 and 334 described above. Grooves 352 and 354 of the second jaw 340 are in alignment with grooves 332 and 334 of the first jaw 320, respectively, for receiving two zip-ties in the aligned grooves between the two jaws. However, the distal end of second jaw 340 does not include the recesses described above, since tail portion of the zip-ties is placed into grooves 352 and 354. In the second jaw, the grooves may have different depths toward distal end 344. As can be appreciated, to engage the tail end of a zip-tie with the head of the zip-tie disposed within recess 333 or 335 at the distal end of jaw 320, the distal ends of grooves 352 and 354 are deeper to ensure alignment between the tail and the passage in the head of the zip-tie, which can be viewed in FIG. 25. It should be understood that the structures of the two opposing jaws described above can be reversed. In other words, jaw 340 may have the recesses and jaw 320 may have the complimentary structure for head-tail engagement of the zip-ties.

In the embodiment shown, each jaw has two grooves for receiving two surgical zip-ties and applying them around a tubular organ. However, each jaw may also have only one groove for receiving and applying a single zip-tie. This may occur in a situation where a single tie is first applied immediately next to a tumor to prevent spreading of cancer cells, prior to applying double zip-ties for dissecting the tubular organ as described above. Furthermore, each jaw may also have four grooves along inner surface 326 of the jaw. This configuration may be used to fasten two pairs of zip-ties, with each pair on one side of the dissecting site. In this case, the first and second grooves may be immediately next to each other, so are the third and fourth grooves; and the cut-distance is positioned between the inner grooves, namely the second and third grooves. Moreover, each jaw may also have three grooves. In this configuration, one groove is on one side and two grooves immediately adjacent to each other are on the other side, with the cut-distance therebetween. The cut-distance can be either positioned between the first and the second grooves, or positioned between the second and the third grooves.

Figure 24:
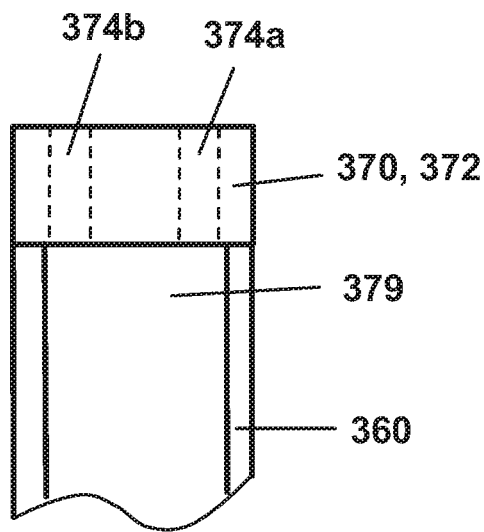
FIG. 24 is an illustrative top view showing a chuck of the tie gripping member in the channel underneath the grooves in the lower jaw shown in FIG. 23.
Figure 24A:
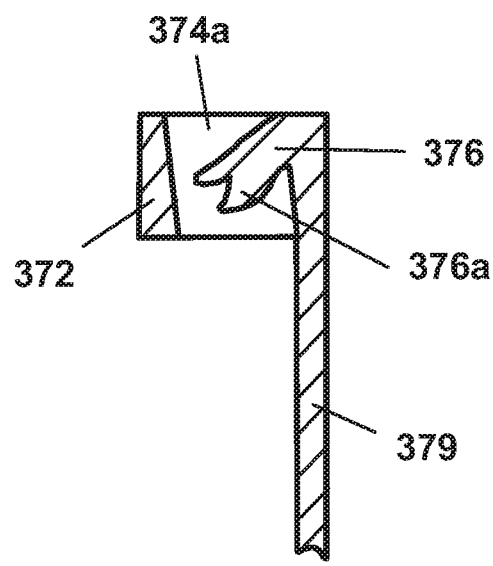
FIG. 24A is a cross-sectional view of the chuck shown in FIG. 24, taken along one passage of the chuck.

The string fastening mechanism can be designed and integrated into the surgical string applicator in various different ways, which is illustrated hereinafter in reference to exemplary embodiments. In one embodiment, the string fastening mechanism comprises a tie gripping member disposed within one of the jaws adapted to grip a portion of a zip-tie placed within the jaws and a tightening mechanism adapted to fasten the gripped zip-tie. In one exemplary embodiment shown in FIGS. 23-23B, the first jaw 320 further includes channel 360 underneath grooves 332 and 334, and a tie gripping member 370 is disposed at the distal end of channel 360 (also see FIG. 24). The distal end of channel 360 is closed, except the openings 333a and 335a which connects channel 360 with recesses 333 and 335. In one embodiment as shown in FIGS. 24 and 24A, tie gripping member 370 comprises a chuck 372 that includes two passages 374a and 374b therethrough, and within each of the passages a barb 376 having one or more barb teeth 376a as shown in FIG. 24A. As can be appreciated, the engagement and interlocking mechanism of chuck 372 with a zip-tie are the same as those between the tail and the head of a zip-tie. Chuck 372 is positioned at the distal end of channel 360 with the opening of passages 374a and 374b facing and aligned with the openings 333a and 335a. Chuck 372 is connected to the tightening mechanism that includes an interface member 202 and a driving mechanism 240 disposed within elongated shaft 210 and handle portion 230. In one embodiment, tie gripping member 370 further includes a strap 379 with one end connected to chuck 372 and the opposing end coupled to the driving mechanism through the interface member. Chuck 372 can be moved from the distal end toward the proximal end of channel 360 by the driving mechanism.

In one embodiment, the interface member 202 is a releasable clamping element, such as a spring-loaded clamp or other suitable mechanical gripping mechanisms, disposed inside the distal end of shaft 210, which clamps strap 379. The driving mechanism 240 includes a motor and a power supply disposed in the handle portion 230 and a connection means disposed in shaft 210, such as a rod, gears, or other suitable means, which interconnects the clamping element and the motor. The driving mechanism pulls the clamped strap 379 in the direction toward the proximal end of the shaft. Once the zip-tie is fastened, the clamping element is opened by a control mechanism in the handle portion to release the strap. Alternatively, if the surgical string applicator is manually operated, the chuck can be moved through the connection means by manual mechanical drive operated by the handle portion.

As can be appreciated, instead of a single chuck, tie gripping member 370 can include two chucks, each thereof including a passage therethrough and a barb disposed within the passage. Each chuck is connected to a strap, which is then coupled to the driving mechanism. Alternatively, the two chucks are bridged together, and a single strap is connected to the bridged chucks. Moreover, in an alternative embodiment chuck 372 is connected to a gear that is coupled with a gear rack provided in channel 360, and the gear is driven by the driving mechanism in the shaft and the handle portion. In this configuration, the gear and gear rack may also be coupled to the interface member of the driving mechanism.

Figure 25C:
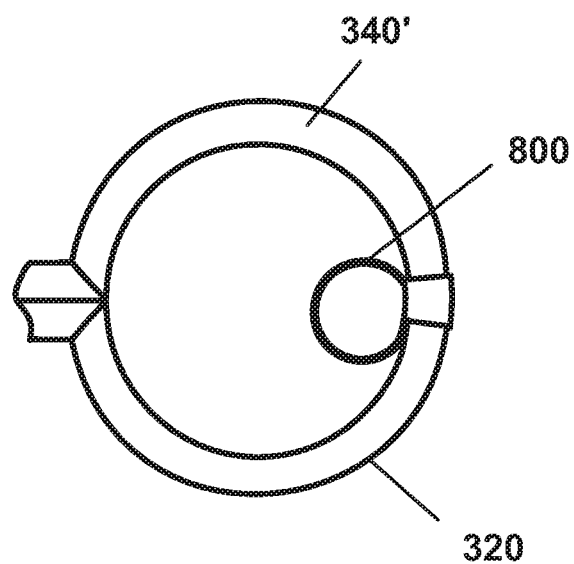
FIG. 25C shows the zip-ties being fastened within the closed jaws shown in FIG. 25.
Figure 25:
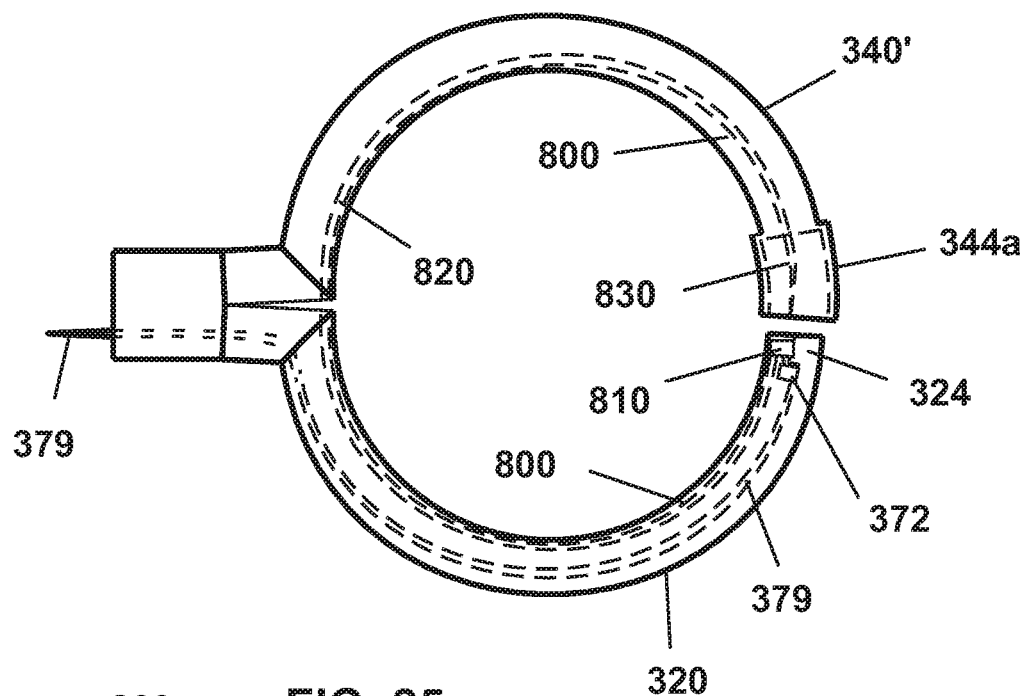
FIG. 25 is an illustrative side view of the jaws, showing the zip-ties and the tie gripping member including the chuck and the belt within the jaws before the jaws are completely closed.
Figure 25A:
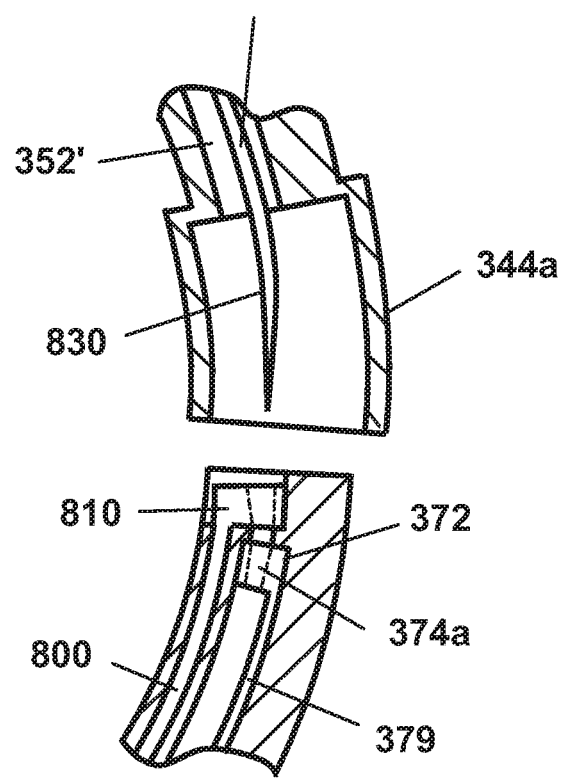
FIGS. 25A and 25B are enlarged views of the distal ends of the two jaws in FIG. 25, showing the distal ends of the jaws before and after complete closing of the jaws.

When in use, two zip-ties 800 are placed into and along the two grooves of the jaws, with their heads 810 disposed at the distal end of one jaw and their tails 830 disposed at the distal end of the opposing jaw, see FIG. 25. Zip-tie 800 has the gear rack on one side of belt portion 820 and also on one side of tail 830. Heads 810 of the two zip-ties are above chuck 372, with the passage within the first head aligned with passages 374a and the passage within the second head aligned with passage 374b of chuck 372, respectively, see FIG. 25A (only one head is shown in the cross-sectional view). When jaws are closed by a control mechanism in the handle portion, the tail 830 of the first zip-tie is caused to insert into head 810 of the first zip-tie and further into passage 374a of chuck 372 underneath, and the tail of the second zip-tie is caused to insert into the head of the second zip-tie and further into passage 374b of chuck 372, respectively, see FIG. 25B (only one head is shown in the cross-sectional view). As such, the engagement between the gear rack on the tail 830 of zip-ties 800 and barb teeth of chuck 372 locks tails 830 of the zip-ties into chuck 372. Then, the driving mechanism is actuated to pull chuck 372, together with tails 830 locked therein, from the distal end 324 of jaw 320 toward the proximal end 322, which results in fastening of zip-ties 800, as illustrated in FIG. 25C. As can be appreciated, the gear rack can be on either side of tail 830, so long as chuck 372 is orientated in the mutual locking direction. As can be further appreciated, alternatively other gripping mechanisms may also be used in lieu of the chuck described above.

Figure 25B:
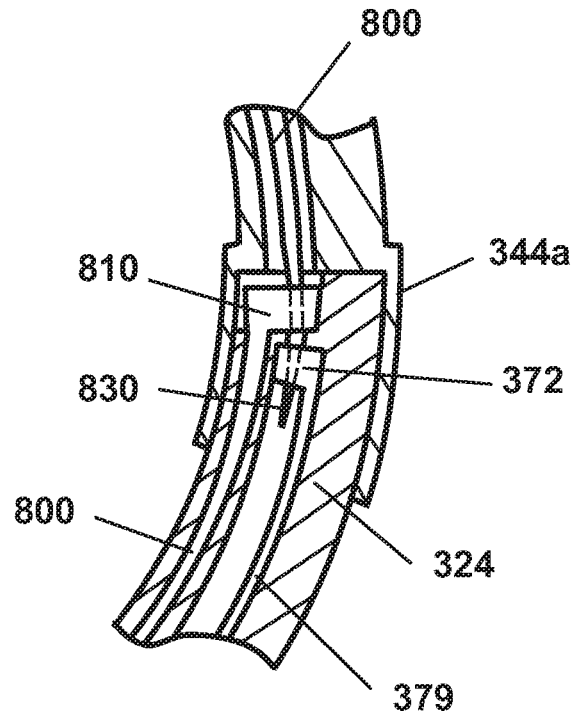

Different mechanisms can be used to facilitate initial engagement of the tail and the head of the zip-tie. In one exemplary embodiment as illustrated in FIGS. 25-25B, the distal ends of the curved jaws are so configured that when the jaws move from an open position to the close position, the tail and head of the zip-tie become engaged with the closing movement. As shown in FIG. 25, the first jaw 320 is a semicircle about 180 degree and has the structures described above, while the second jaw 340' is a semicircle about 200 degree, including a protruding segment 344a at the distal end of the jaw. As shown in FIGS. 25 and 25B, protruding segment 344a has a dimension slightly larger than, and complementary to, the distal end 324 of the first jaw 320. As shown in FIG. 25, when a zip-tie 800 is placed into the grooves, tail 830 is disposed within protruding segment 344a of the second jaw 340', which extends out from groove 352'. As illustrated in FIG. 25B, with this configuration when the second jaw 340' is brought to a complete closed position against the first jaw 320, protruding segment 344a of the second jaw 340' extends into the region of, and overlaps with, the distal end 324 of the first jaw 320. This extended move brings the tail 830 of the zip-tie forward and causes the tail 830 entering into head 810 disposed at the distal end 324 of the first jaw 320, and further entering into chuck 372 of the tie gripping member, as described above. In an alternative embodiment, the protruding segment 344a of the second jaw is not present, only the tail of the zip-tie is placed extending beyond the grooves in the same manner shown in FIGS. 25 and 25A. As can be appreciated, with either configuration the zip-tie used has a length greater than the circumferential length of the inner loop formed by the two jaws.

In a further alternative embodiment, both first and second jaws are semicircles about 180 degree, when a zip-tie is placed into the grooves, the tail of the zip-tie flushes with the distal end of the groove of the second jaw. In this configuration, the string applying assembly further comprises a tie advancing mechanism 302 disposed within the second jaw, on the side of or underneath the groove. The tie advancing mechanism 302 includes a grasping member adapted to engage with either the belt or the tail portion of the zip-tie. As can be appreciated, in this embodiment the tail may have surface textures facilitating engagement with the grasping member. The tie advancing mechanism can be actuated by a second driving mechanism disposed in elongated shaft 210 and handle portion 230. When in use, the first and second jaws are brought into a complete closed position, with their distal ends against each other. Then, the tie advancing mechanism is actuated, which engages the belt portion or the tail portion of the zip-ties and pushes the tail forward toward the distal end of the first jaw, which causes the tail entering into the head and into the chuck of the tie gripping member described above. With this configuration, the zip-tie used may have a length equivalent to the circumferential length of the jaws.

The string fastening mechanism of the surgical string applicator is described in reference to the exemplary embodiment that has two parallel grooves within the jaws. However, as can be understood by those of ordinary skill in the art that the same mechanism can be used for the jaws that includes only one or more than two grooves. In those configurations, the chuck of the tie gripping member includes the number of passages corresponding to the number of grooves. Alternatively, different number of chucks may be provided corresponding to the number of grooves.

Figure 26:
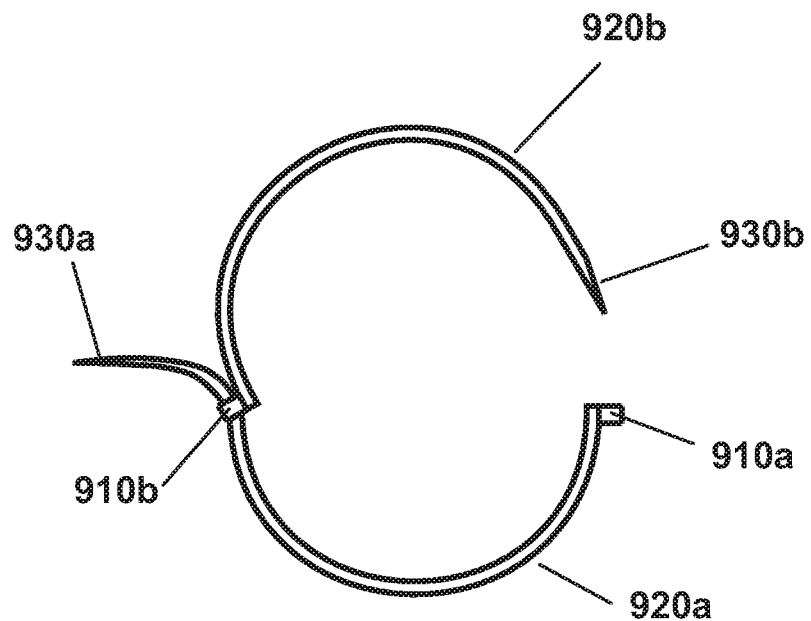
FIG. 26 is an illustrative view showing the relationship between two head-tail connected zip-ties when they are placed into the grooves of opened jaws (not shown) in one embodiment of the present invention.

In another exemplary embodiment, a different approach is used to fasten the zip-ties. For simplicity, the structure and mechanism are described in reference to only one groove in each of the first and second jaws. In this configuration, the groove structure can be the same as those described above and the string fastening mechanism can have the same tightening mechanism described above; however, the tie gripping member as wells as the channel underneath the groove for placing and moving the tie gripping member are not present. As illustrated in FIG. 26, in this embodiment two shorter and mutually connected zip-ties 920a and 920b are used to facilitate fastening a tubular organ received within the jaws. Each of zip-ties 920a and 920b has a length similar to, or greater than, the longitudinal length of one jaw, and the two zip-ties may have a same or different length. As shown, the first zip-tie 920a has a head 910a and a tail 930a, and the second zip-tie 920b has a head 910b and a tail 930b. Before placing them into the jaws, the tail 930a of the first zip-tie 920a is inserted and locked into the head 910b of the second zip-tie 920b. This forms a head-tail connection between the two zip-ties, hence, zip-ties 920a and 920b are herein referred to as head-tail connected zip-ties. When the connected zip-ties 920a and 920b are placed into the jaws, head 910a of the first zip-tie 920a is positioned at the distal end of the first jaw and tail 930b of the second zip-tie 920b is positioned at the distal end of the second jaw, with the orientation illustrated in FIG. 26 without showing the jaws. As such, the mutually joined head 910b of the second zip-tie 920b and the tail 930a of the first zip-tie 920a are located at the proximal ends of the jaws, next to the distal end 214 of shaft 210. In this embodiment, the tail 930a of the first zip-tie 920a is inserted into and locked by the claiming element of the tightening mechanism, disposed inside the distal end 214 of shaft 210 as described above. The driving mechanism pulls the tail 930a of the first zip-tie 920a in the direction toward the proximal end of the shaft. Once the loop formed by the two head-tail connected zip-ties is fastened, the clamping element is opened to release the tail 930a of the first zip-tie 920a.

When in use, a tubular organ is received between the first and second jaws and the jaws are closed by the control mechanism in the handle portion as described above. The initial engagement between the tail 930b of the second zip-tie 920b with the head 910a of the first zip-tie 920a can be effected using the same mechanisms described above. In one embodiment shown in FIG. 27, the first jaw 320' has same structures of jaw 320 described above, but without channel 360, and the distal end of the second jaw 340' has the same structures shown in FIG. 25, wherein the tail 930b of the second zip-tie 920b is extended beyond the groove. When the second jaw is brought into a complete closed position, the tail 930b of the second zip-tie 920b is caused to enter into the head 910a of the first zip-tie 920a (see FIG. 26). It is noted that in this case the tail 930b of the second zip-tie 920b may extend in a lesser degree beyond the groove, since the tail 930b only engages with the head of the first zip-tie, but not with the chuck of the tie gripping member. In another embodiment, a tie advancing mechanism disposed in the second jaw can be used to facilitate the initial engagement between the tail 930b of the second zip-tie 920b and the head 910a of the first zip-tie 920a, as described above.

Figure 27:
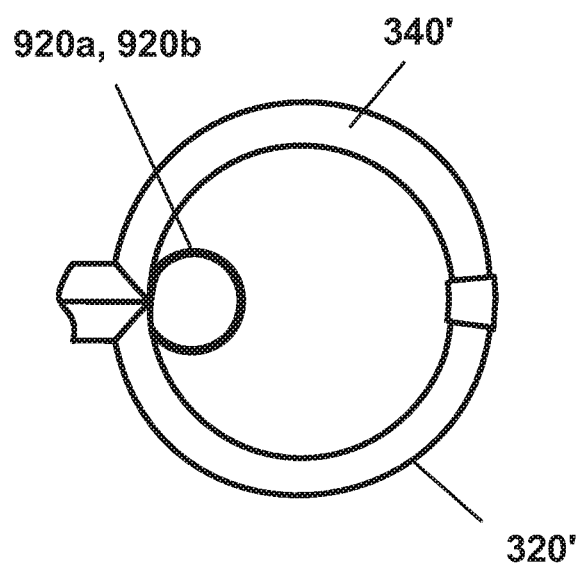
FIG. 27 shows the loop formed between the two head-tail connected zip-ties shown in FIG. 26 being fastened within the closed jaws.

After the tail 930b of the second zip-tie 920b is locked into the head 910a of the first zip-tie 920a, the tightening mechanism can be actuated using a trigger on the handle portion. The driving mechanism pulls the clamping element, together with the tail 930a of the first zip-tie 920a locked therein, toward proximal end of the elongated shaft. This results in fastening of the loop formed by the two zip-ties within the jaws 340' and 320', as shown in FIG. 27.

In a further embodiment, optionally the surgical string applicator further includes a blade disposed within one of the jaws. In one exemplary embodiment, the blade 304 is positioned within a recess in the ridge 310 between the grooves in one of the jaws. The blade 304 is disposed along the longitudinal axis of the jaw, preferably, at the center between the two grooves. Moreover, the blade is positioned adjacent to the position of the head of zip-tie within the jaw, since the tissue is fastened against the head. In other words, in the embodiment where a zip-tie is fastened against its own head at the distal end of the jaw as illustrated in FIG. 25C, the blade is disposed at the distal end of a jaw. However, in the other embodiment where two head-tail connected zip-ties are used and the loop is fastened at the proximal ends of the jaws (see FIG. 27), the blade is disposed at the proximal end of a jaw. One end of the blade can be pivotally attached to the lower portion of the recess, when being actuated the blade rotates around the pivot point, which cuts the tissue between two fastened zip-ties. Prior to actuation, the blade is hidden completely within the ridge. The length of the blade is sufficient to dissect the tubular organ fastened by the zip-ties, and the blade can be straight or curved depending on the shape of the jaws and the position of the blade. The blade can be actuated by a control mechanism in the handle portion 230. Moreover, the surgical string applicator may further include a second blade disposed within one of the jaws for cutting the zip-tie adjacent the head thereof after fastening the zip-tie. The second blade can be disposed at either the distal end or proximal end of the jaws, depending on the location where the zip-tie is fastened as described above. In the embodiment shown in FIG. 27, the second blade can also be disposed in the distal end of the elongated shaft. The second blade is positioned to cut the zip-tie in the direction transverse to the longitudinal axis of the jaws.

The string fastening mechanism of the surgical string applicators are described above in particular reference to applying zip-ties that have a self-locking mechanism. However, as can be appreciated, the surgical string applicators of the present invention can also be structured to apply other surgical strings that do not have a self-locking mechanism. For example, the distal end of one jaw may have openings complementary to the tail of the surgical strings disposed at the distal end of the opposing jaw, to receive the tail portion of the surgical strings when the jaws are brought into closed position (similar to openings 333a and 335a in FIG. 23B). The inserted tail of a surgical string can be gripped by a gripping means adjacent the openings and tightened at distal end in a manner similar to those described above, then the overlapping portion of the tightened surgical string can be joined by a fasten means, such as clamp, locking pin, surgical glue or other suitable means, applied within the jaw where the overlapping portion is in. It is further noted that the structural components for facilitating engagement of different portions of a surgical string can also be placed at the proximal ends of the opposing jaws, when the jaws open and close at their proximal ends as illustrated in the embodiment shown in FIG. 29B.

Handle portion 230 can assume any ergonomic shape or geometry that can be held and operated by one hand. Handle portion can include one or more triggers coupled thereto for opening and closing the jaws, and actuating the string fastening mechanism. In the embodiment shown in FIG. 21, a first trigger 232 movably coupled to handle 230 for opening or closing the opposed jaws 320 and 340, and locking the jaws at a selected position. First trigger 232 can be pulled or pushed laterally to effect opening or closing of the jaws. Alternatively, two separate triggers can be used to effect opening or closing of the jaws. For opening and closing the curved jaws, various known mechanisms used for opening and closing linear surgical staplers can be used for the purpose of the present invention. In one exemplary embodiment, actuation of first trigger 232 is effective to slide a closure tube over proximal ends 322, 342 of jaws 320, 340 to close the jaws, or to slide the closure tube away from the proximal ends to open the jaws. Handle portion 230 further includes a second trigger 234 movably coupled thereto for actuating the string fastening mechanism. The second trigger, or an additional trigger (not shown), may also be effective to actuate the blade. While not shown, handle portion 230 can additionally or alternatively include triggers, rotatable knob, lever, sliding knob, or other mechanisms for opening and closing the jaws, articulating the jaws, rotating the elongated shaft, actuating the string fastening mechanism, and actuating the blades. These triggers are jointly referred to as control mechanisms, which can be powered by the power supply such as a battery enclosed in the handle portion. Alternatively, the triggers can also be activated manually.

In one embodiment, the pair of jaws of the surgical string applicator can be hinged together as a module, which can be attached to or removed from the elongated shaft. Moreover, the entire module can be disposable, which is provided as a sterilized package, with zip-ties preloaded within the grooves. Alternatively, the inner side of the jaws including the components described above can be provided as a disposable cartridge with zip-ties preloaded within the grooves, while the outer shells of the jaws remain attached to the shaft. The cartridge, provided as a sterilized package, can be placed into outer shells of the jaws by the surgeon. In either case, when the disposable jaw module is attached to the shaft, or the cartridge is placed into the outer shells of the jaws, the strap of the tie gripping member is locked into the releasable interface member described above, which is coupled to the driving mechanism. In the embodiment where two head-tail connected zip-ties are used, the tail 930a of the first zip-tie 930 is locked into the releasable interface member as described above.

In surgical string applicator 200 described above, the two curved jaws are aligned with the elongated shaft. However, it should be understood that the pair of jaws can also have different orientation relative to the shaft. FIG. 28 illustrates a surgical string applicator 400 in a further embodiment of the present invention. In this embodiment, the two curved jaws 420 and 440 are disposed transverse or perpendicular to elongated shaft 410. In either embodiment, the pair of jaws can be articulated to position the jaws at various angles relative to the elongate shaft. Moreover, the elongated shaft can be rotated 360 degrees, which facilitates positioning of the jaws relative to the subject tubular organ. The handle portion can further include one or more triggers for articulating the pair of jaws relative to the elongate shaft and for rotating the shaft. Various driving mechanisms for articulating the jaws or a head group relative to the shaft and rotation of the shaft have been used in linear surgical staplers, which can be used for the same purpose in the surgical string applicator of the present invention.

FIG. 29 further illustrates a surgical string applicator 500 in another embodiment of the present invention. As shown, the curved jaws 520 and 540 have a substantially less curvature than the jaws in surgical string applicator 200, and the closed jaws 520 and 540 exhibit an elliptical shape. These elongated curved jaws are particularly suitable for laparoscopic surgery. In one exemplary embodiment, the jaws have a length from about 30 mm to about 80 mm, a width equal or less than 12 mm, and an outer cross-width of the two jaws equal or less than 12 mm. With such a small dimension, the jaws can be introduced into the body through a cannula, or trocar currently used in laparoscopic surgeries. For surgical string applicator 500, shaft 510 may have a diameter from about 8 mm to about 12 mm, and a length from about 250 mm to about 400 mm, which also depend on the shape and length of handle portion 530. The structures of the grooves, the string fastening mechanism and the control mechanism described above can also be used with surgical string applicator 500.

In one exemplary embodiment as shown in FIG. 29A, the first jaw 520 is fixed and the second jaw 540 can be pivoted at its proximal end 542, which effects opening or closing of the distal end 544 of the second jaw relative to the distal end 524 of the first jaw. Alternatively, the second jaw 540 may be fixed and the first jaw 520 may be pivoted at its proximal end 522.

In a further exemplary embodiment as shown in FIG. 29B, the first jaw 520' is fixed and the second jaw 540' has its distal end 544' pivotally connected to the distal end 524' of the first jaw. FIG. 29B shows the two elongated jaws in a completely open position, in which the distal ends 524' and 544' and proximal ends 522' and 542' of the first and second jaws are all on the same plane, with the two proximal ends 522' and 542' disposed at two opposing ends. With this embodiment, when in use, the jaws can be inserted through a trocar into the body at its complete open position shown in FIG. 29B. Then, after placing the subject tubular organ on the inner surface of the jaws, the second jaw is actuated by a control mechanism in the handle to rotate the second jaw around the pivoted distal end 544', as indicated by the arrow in FIG. 29B, which closes the proximal end 542' of the second jaw against the proximal end 522' of the first jaw. When retrieving the jaws from the body, the second jaw is opened again to the complete open position, and the jaws are pulled back through the trocar. As can be appreciated, this configuration is more advantageous for laparoscopic surgery, because the completely opened jaws may have only about half of the outer cross-width of the closed jaws shown in FIG. 29, as such each elongated jaws may have more dimension in thickness for conveniently placing desired groove structure, channel, tie gripping member, or tie advancing mechanism in the jaws as described above. This reduces technical difficulties in design and manufacturing the surgical string applicator for laparoscopic surgery.

In the embodiment shown in FIG. 29B, the first jaw 520' faces up and the second jaw 540' closes downwardly. Alternatively, the first jaw may face down and the second jaw closes upwardly. Moreover, the elongated shaft can rotate for 360 degree, which positions the first and second jaws at any desirable orientation.

Moreover, in a further embodiment a tie advancing mechanism can disposed within the elongated shaft. With this configuration, one or more zip-ties are placed in the elongated shaft 510', and the tie advancing mechanism is adapted to advance the zip-ties into the grooves in the opened jaws 520' and 540'. Alternatively, one or more zip-ties are placed partially in the shaft and partially in the first jaw, and the tie advancing mechanism is adapted to advance the zip-ties from the first jaw 520' into the second jaw 540'.

Figure 30:
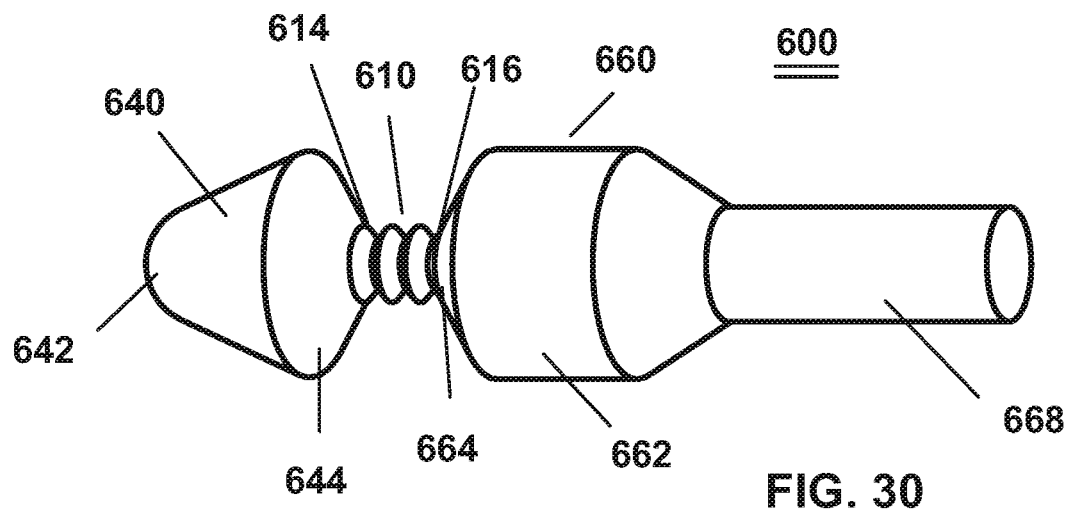
FIG. 30 is a perspective view of an intra-rectal guide in one embodiment of the present invention.
Figure 31:
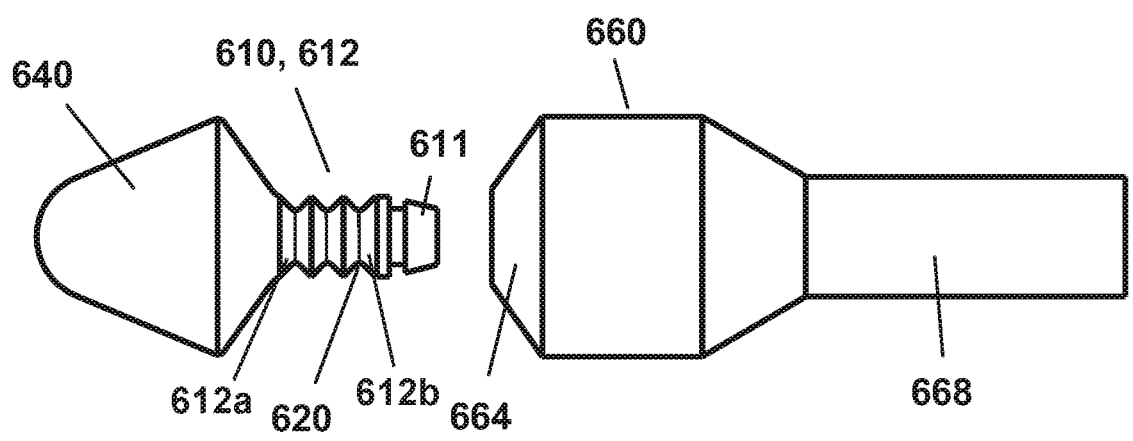
FIG. 31 is an exploded side view of the intra-rectal guide shown in FIG. 30.

In a further aspect, the present invention further provides an intra-lumenal position guide to be used together with the surgical string applicator described above for anastomosis surgery, which assists positioning of the zip-ties and guiding the circular stapler used in the surgery. Referring now to FIGS. 30-33, in one embodiment the present invention provides an intra-rectal guide 600 for colorectal anastomosis surgery. As shown in FIGS. 30 and 31, intra-rectal guide 600 includes a guide section 610 having a distal end 614 connected to a lead member 640, and a proximal end 616 detachably connected to a proximal handle member 660. The lead member 640, guide section 610 and proximal handle member 660 are coaxial.

Lead member 640 has a conical front end 642 and a rear surface 644 connected to guide section 610. Preferably, rear surface 644 is inclined, forming a convex rear surface; however, rear surface 644 can also be planar. Handle member 660 includes a front cylindrical section 662 with a front surface 664 detachably connected to guide section 610 and a circumferentially inclined section connecting to circular shaft 668 that has a substantially smaller diameter than the front cylindrical section 662. Preferably, front surface 664 is also inclined, forming a convex front surface; however, the front surface can also be planar. In one exemplary embodiment, the slope of the inclined rear surface 644 of lead member 640 and the inclined front surface 664 of handle member 660 is same, which forms a tapered entrance for the jaws of a surgical string applicator described above to enclose around the guide section 610. Both lead member 640 and proximal handle member 660 have smooth outer surfaces which are in direct contact with the tissue when the guide is used. Lead member 640 and proximal handle member 660 may have a same outer diameter.

Guide section 610 has a length between lead member 640 and handle member 660 equivalent or greater than the width of the jaws of the surgical string applicator described above, which permits closing the jaws of a surgical string applicator around guide section 610. The length of guide section 610 can be typically from about 5 mm to about 30 mm; however, it may vary depend on the width of the jaws of the surgical string applicator. The guide section has a diameter less than the diameter of the inner loop formed by closed jaws of a surgical string applicator, as the zip-ties are fastened around the guide section as described hereinafter. As an intra-rectal guide, guide section 610 has a diameter greater than the center rod of circular staplers used in colorectal anastomosis surgery. In one exemplary embodiment, guide section 610 has a diameter from about 13 mm to about 17 mm. Moreover, as an intra-rectal guide lead member 640 and proximal handle member 660 can typically have an outer diameter from about 20 mm to about 33 mm, preferably from about 28 mm to about 31 mm. The lead member 640 of an intra-rectal guide may have a length from about 16 mm to about 24 mm. The circular shaft 668 of the handle member may have an extendable length, which may be adjusted according to the distance of the dissecting site from the anus. As can be appreciated, the above dimensions are given as an example in reference to an intra-rectal guide, and for a smaller tubular organ the corresponding dimensions may be smaller or different.

Figure 31A:
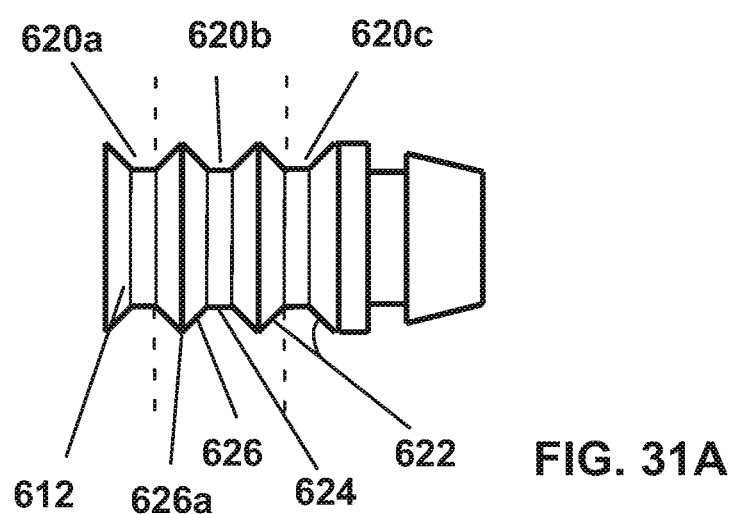
FIG. 31A is an enlarged side view of the guide section.

The guide section 610 includes a cylindrical body 612. In the exemplary embodiment shown, there are multiple parallel grooves 620 (620a-620c) disposed circumferentially around the cylindrical body. As shown in FIGS. 31 and 31A, each of the grooves has tapered side walls 622 and a bottom 624. The bottom 624 of groove 620 is preferably planar for seating a zip-tie and has a width equal or greater than the width of a zip-tie to be applied by the surgical string applicator. Preferably, groove 620 has a depth greater than the thickness of a zip-tie, and the crest 626a of ridge 626 between two adjacent grooves has a narrow width, which is substantially less than the width of a zip-tie. In the specific embodiment shown, the distance between grooves 620a and 620c, between the closest points at the bottoms as shown by the broken lines in FIG. 31A, corresponds to the cut-distance between the grooves in the jaws of the surgical string applicator. As such, when intra-rectal guide 600 is used together with a surgical string applicator, cylindrical body 612 is cut at groove 620b. It should be understood that in addition to the grooved structure described above, the cylindrical body may have other suitable surface structures. In one alternative embodiment, the cylindrical body has only two grooves 620a and 620c, without the center groove 620b. In another alternative embodiment, the cylindrical body has a micro-textured or rough surface without above described grooves. Instead of fixed grooves, micro-textured surface can also prevent slipping of the tubular organ.

As further shown in FIG. 31, cylindrical body 612 has a connection interface 611 at its proximal end 616, which is adapted to insert and lock into a releasable locking mechanism disposed about the center of front surface 664 of handle member 660. The handle member 660 can be detached from cylindrical body 612 using the releasable locking mechanism, during a surgical procedure as described hereinafter. Various releasable mechanical interlocking mechanisms can be used between the guide section and the handle member for the purpose of the present invention. In an exemplary embodiment shown, a quick lock is used, which locks the connection interface 611 automatically when it is inserted and releases the connection interface by a control mechanism in the shaft 668.

The lead member 640 and handle member 660 can be made of metal, silicone, plastics, or other rigid materials suitable for surgical use. The cylindrical body 612 of the guide section can be made of a rigid material such as polymeric foam board that can be cut and pierced. Alternatively, the cylindrical body may include two layers. The outer shell, including the grooves, can be made of a rigid material that can be cut, and the center can be made of a soft material that can be pierced by the center rod of a circular stapler.

The use of the intra-lumenal position guide together with the surgical string applicator in a zip-tied anastomosis surgery described above is illustrated now in reference to a colorectal anastomosis surgery with intra-rectal guide 600 and surgical string applicator 200. In the surgical procedure, intra-rectal guide 600 is first inserted into the rectum through the anus with guide section 610 positioned at the planned dissecting site. Then, opened jaws of surgical string applicator 200 are placed in the space between lead member 640 and handle member 660 of intra-rectal guide 600, and are then completely closed around the rectum with the guide section 610 inside. At this time, the handle member 660 is released from guide section 610, and retrieved from the anus. Then, the tightening mechanism of the surgical string applicator is actuated to fasten the two zip-ties placed in the grooves of the jaws. When the zip-ties are being tightened around the rectum, they are fastened into the grooves 620a and 620c of intra-rectal guide 600. The two ridges between these two grooves maintain the cut-distance between the two parallel zip-ties. Then, the blade in the surgical string applicator is triggered to cut through the tissue and cylindrical body 612 at the center groove 620b between the two fastened zip-ties.

After the cut, the front portion 612a of cylindrical body 612 and lead member 640 are sealed inside the divided colon. The divided colon is taken away from the dissecting site to remove tumor or other abnormalities. As described above in the zip-tied colorectal anastomosis surgery, after removal of the abnormal segment, the anvil of a circular stapler is placed into the resected end of the colon and the resected end is closed again by a zip-tie, as shown in FIGS. 5 and 17.

Figure 32:
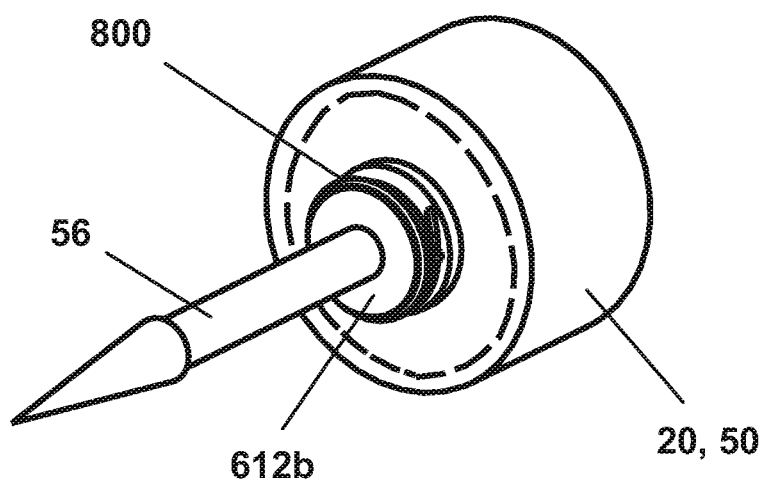
FIG. 32 is an illustrative view, showing the center rod of the head of the circular stapler perforating through the rear portion of the guide section of the intra-rectal guide.
Figure 33:
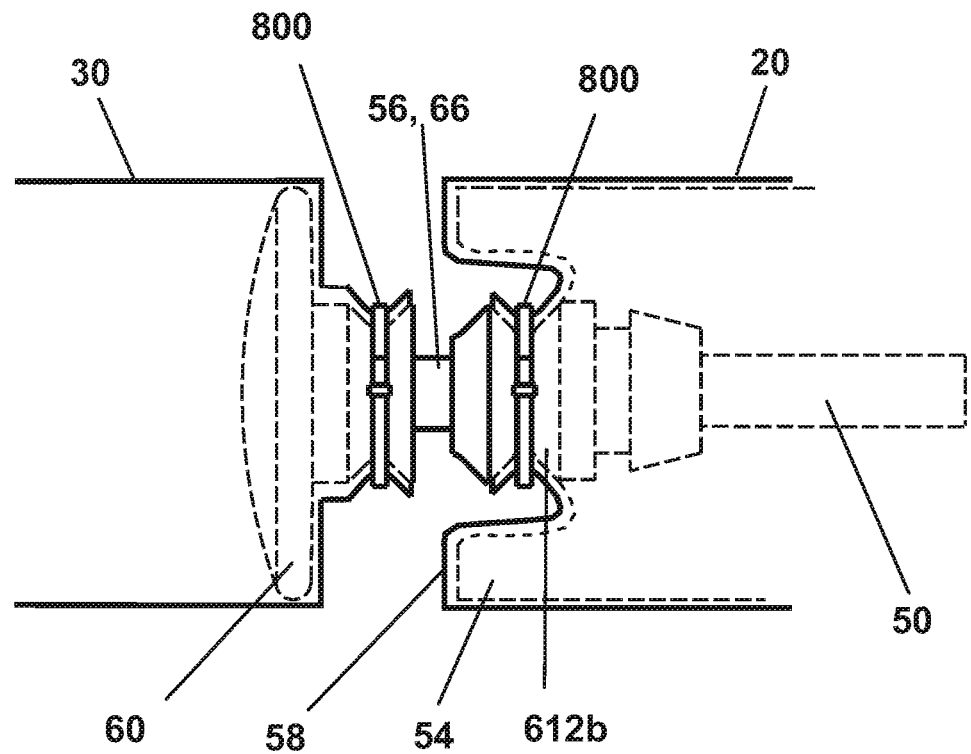
FIG. 33 is an illustrative view showing the zip-tied colon joined by the anvil to the zip-tied rectum, with the rear portion of the guide section of the intra-rectal guide remained around the center rod of the circular stapler.

On the other side, a rear portion 612b of cylindrical body 612 is sealed inside the divided rectum portion. When removal of abnormal segment is complete and the resected end is closed again by a zip-tie as described above, the head member of the circular stapler is inserted into the rectum through the anus, and placed against the rear portion 612b of cylindrical body 612 of the intra-rectal guide. As illustrated in FIG. 32, the center rod 56 of the circular stapler 50 is advanced, which perforates the rear portion 612b and extends out from the zip-tied rectum 20. Then, the anvil shaft 66 and the center rod 56 are joined and pulled together, as illustrated in FIG. 33. As shown, the rear portion 612b of cylindrical body 612 is around the center rod 56, which does not obstruct the staples disposed along the periphery of cartridge 54. Therefore, the front end 58 of cartridge 54 of circular stapler 50 is pulled against anvil 60, and the stapler is actuated to staple the colon 30 and the rectum 20 together as described above.

As can be appreciated, the method of using the intra-rectal guide together with the surgical string applicator in the colorectal anastomosis surgery has several advantages. Using the intra-rectal guide, the zip-ties are fastened within the grooves in the guide section, and the grooves prevent any lateral movement of the zip-ties on the slippery tissue. On the other hand, the cylindrical body of the intra-rectal guide creates a central guide within the zip-tied tissue, which directs a central positioning of the center rod of the circular stapler. As such, when the center rod of the circular stapler perforates the cylindrical body, it assures the desired central alignment between the zip-tied rectum and the zip-tied colon. Therefore, with the assistance of the intra-rectal guide, quality and safety of the zip-tied anastomosis surgery method can be further improved.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A surgical string applicator for anastomosis surgery comprising:
    an elongate shaft having proximal and distal ends;
    a string applying assembly comprising first and second opposing jaws connected to said distal end of said elongate shaft and the first and second jaws being configured to close around a tubular organ of the anastomosis surgery, each of the first and second jaws having one or more grooves along an inner surface of the first and second jaws, wherein said one or more grooves extend from a distal end to a proximal end of each of the first and second jaws, and each of the first and second jaws having an opening at the distal end thereof; at least one surgical string housed in the first and second jaws within said one or more grooves of the first and second jaws in a form of an open loop with one end of the at least one surgical string at the distal end of the second jaw and an opposing end of the at least one surgical string at the distal end of the first jaw; and a string fastening mechanism adapted to engage and fasten the at least one surgical string around the tubular organ, wherein said string fastening mechanism comprises a tie gripping member disposed within the first jaw configured to grip said one end of the at least one surgical string extended into the opening of the first jaw from the second jaw when the first and second jaws are configured to be closed around the tubular organ such that the at least one surgical string is configured to encircle the tubular organ, and the string fastening mechanism is configured to tighten the at least one surgical string around the tubular organ; and
    a handle portion connected to said proximal end of said elongate shaft; said handle portion including one or more triggers configured to open and close at least one of the first and second jaws, and to actuate said string fastening mechanism.

2. The surgical string applicator of claim 1, wherein said proximal ends of said first and second jaws are connected to said distal end of said elongate shaft, and at least one of said first and second jaws pivots at said proximal end thereof.

3. The surgical string applicator of claim 1, wherein said first and second jaws articulate relative to, and rotate about, a longitudinal axis of said elongate shaft.

4. The surgical string applicator of claim 1, wherein said string fastening mechanism is configured to drive said tie gripping member along a portion of the first jaw.

5. The surgical string applicator of claim 1, wherein said string fastening mechanism is configured to tighten the tubular organ to the distal ends of the first and second jaws.

6. The surgical string applicator of claim 1, wherein said first and second jaws are configured that when said first and second jaws move from an open position to a closed position, said one end of said at least one surgical string disposed at the distal end of the second jaw is caused to enter into said opening at the distal end of the first jaw.

7. The surgical string applicator of claim 1, wherein said string applying assembly is configured to advance said one end of said at least one surgical string for entering into said opening at the distal end of the first jaw.

8. The surgical string applicator of claim 1, wherein said one or more grooves includes two grooves parallel with each other and with a predetermined distance therebetween.

9. The surgical string applicator of claim 8, wherein said at least one surgical string includes two surgical strings, each of the two surgical strings disposed within a respective one of said two grooves with said one end of each surgical string of the two surgical strings disposed in the distal end of the second jaw and said opposing end of each surgical string of the two surgical strings disposed in the distal end of the first jaw.

10. The surgical string applicator of claim 1, wherein the surgical string applicator is configured to dissect tissue fastened by said at least one surgical string.

11. The surgical string applicator of claim 1, wherein the string fastening mechanism is configured to pull said tie gripping member gripped on said one end of the at least one surgical string from the distal end of the first jaw toward the proximal end of the first jaw and configured to tighten the at least one surgical string around the tubular organ.

12. A surgical string applicator system for anastomosis surgery comprising
the surgical string applicator of claim 1 and an intra-lumenal position guide, said intra-lumenal position guide comprising a guide section having a distal end connected to a lead member and having a proximal end detachably connected to a proximal handle member;
said guide section including multiple parallel grooves disposed circumferentially.

13. The surgical string applicator system of claim 12, wherein said one or more grooves of the surgical string applicator has two grooves with a predetermined distance therebetween, and a distance between the parallel grooves on the guide section of the intra-lumenal position guide corresponds to the predetermined distance between the two grooves in the first and second jaws of the surgical string applicator for applying the at least one surgical string in the parallel grooves on the guide section of the intra-lumenal position guide.

14. The surgical string applicator system of claim 13, wherein the at least one surgical string of the surgical string applicator comprises two surgical strings, each of the two surgical strings disposed within a respective one of said two grooves with said one end of each surgical string of the two surgical strings disposed in the distal end of the second jaw and said opposing end of each surgical string of the two surgical strings disposed in the distal end of the first jaw.

15. The surgical string applicator system of claim 12, wherein the guide section has a length between the lead member and the proximal handle member equivalent to or greater than a width of the first and second jaws of the surgical string applicator for closing the first and second jaws around the guide section.

* * * * *